United States Patent
Kimoto

(10) Patent No.: US 8,545,398 B2
(45) Date of Patent: Oct. 1, 2013

(54) IN-VIVO IMAGE ACQUIRING APPARATUS, RECEIVING APPARATUS AND IN-VIVO IMAGE ACQUIRING SYSTEM

(75) Inventor: Seiichiro Kimoto, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1445 days.

(21) Appl. No.: 12/138,978

(22) Filed: Jun. 13, 2008

(65) Prior Publication Data

US 2008/0312504 A1 Dec. 18, 2008

(30) Foreign Application Priority Data

Jun. 13, 2007 (JP) .............................. 2007-156741

(51) Int. Cl.
*A61B 1/04* (2006.01)

(52) U.S. Cl.
USPC .......................................... 600/118; 600/109

(58) Field of Classification Search
USPC .............. 600/118, 103, 109, 117, 160, 427, 600/101, 424, 410, 476; 382/107; 607/54; 348/36, 65, 45; 606/14, 33
See application file for complete search history.

(56) References Cited

U.S. PATENT DOCUMENTS

| | | | |
|---|---|---|---|
| 6,904,308 B2 | 6/2005 | Frisch et al. | |
| 2003/0081685 A1* | 5/2003 | Montgomery | 375/240.24 |
| 2003/0213495 A1 | 11/2003 | Fujita et al. | |
| 2005/0043583 A1* | 2/2005 | Killmann et al. | 600/109 |
| 2005/0054897 A1* | 3/2005 | Hashimoto et al. | 600/118 |
| 2005/0159643 A1* | 7/2005 | Zinaty et al. | 600/109 |
| 2005/0187433 A1* | 8/2005 | Horn et al. | 600/160 |
| 2005/0192476 A1* | 9/2005 | Homan et al. | 600/118 |
| 2006/0285756 A1* | 12/2006 | Sugita | 382/232 |
| 2007/0098273 A1* | 5/2007 | Sasaki | 382/232 |
| 2007/0118017 A1 | 5/2007 | Honda | |
| 2007/0142703 A1* | 6/2007 | Lu | 600/109 |
| 2008/0051642 A1* | 2/2008 | Krupnik | 600/302 |
| 2008/0133271 A1* | 6/2008 | Chang | 705/3 |
| 2008/0143822 A1* | 6/2008 | Wang et al. | 348/36 |
| 2008/0187041 A1* | 8/2008 | Utsunomiya et al. | 375/240.01 |
| 2009/0060463 A1* | 3/2009 | Nishio | 386/112 |

FOREIGN PATENT DOCUMENTS

| | | |
|---|---|---|
| EP | 1 769 720 A1 | 4/2007 |
| EP | 1 941 828 A1 | 7/2008 |
| EP | 1 679 029 B1 | 11/2009 |
| JP | 11-112569 | 4/1999 |

(Continued)

OTHER PUBLICATIONS

Japanese Office Action dated Apr. 10, 2012 from corresponding Japanese Patent Application No. JP 2007-156741 together with an English language translation.

*Primary Examiner* — John P Leubecker
*Assistant Examiner* — Ronald D Colque
(74) *Attorney, Agent, or Firm* — Scully, Scott, Murphy & Presser, P.C.

(57) ABSTRACT

An in-vivo image acquiring system includes a capsule endoscope which is introduced into the inside of a subject to acquire an in-vivo image of the subject and a receiving apparatus for receiving the in-vivo images of the subject from the capsule endoscope through receiving antennas. The capsule endoscope transmits the in-vivo images of the subject taken successively at a time interval corresponding to function or feature of the capsule endoscope. The receiving apparatus calculates a time interval of the in-vivo images received successively from the capsule endoscope and identifies the in-vivo images depending on the function or feature of the capsule endoscope based on a calculated time interval.

14 Claims, 20 Drawing Sheets

(56) References Cited

FOREIGN PATENT DOCUMENTS

| | | |
|---|---|---|
| JP | 2003-19111 | 1/2003 |
| JP | 2003-038425 A | 2/2003 |
| JP | 2003-325439 A | 11/2003 |
| JP | 2004-167163 A | 6/2004 |
| JP | 2005-80842 | 3/2005 |
| JP | 2005-143668 A | 6/2005 |
| JP | 2007-21039 A | 2/2007 |
| JP | 2007-98012 A | 4/2007 |
| JP | 2007-130263 A | 5/2007 |
| WO | WO 03/010967 A1 | 2/2003 |
| WO | WO 2005/084521 A1 | 9/2005 |
| WO | WO 2007/043473 A1 | 4/2007 |

* cited by examiner

FIG.19

| COMBINATION OF TIME INTERVAL | FUNCTION UNIQUE TO CAPSULE TYPE ENDOSCOPE | | | | |
|---|---|---|---|---|---|
| | FRAME RATE | ILLUMINATION LIGHT INTENSITY | IMAGE COMPRESSION PROCESSING | NUMBER OF POSSESSED IMAGING UNIT | |
| (t1,t1) | STANDARD VALUE | STANDARD VALUE | NONE | 1 | ← STANDARD MONOCULAR CAPSULE |
| (t2,t3) | STANDARD VALUE | HIGHER THAN STANDARD VALUE | NONE | 1 | ← HIGH ILLUMINATION MONOCULAR CAPSULE |
| (t4,t4) | HIGHER THAN STANDARD VALUE | STANDARD VALUE | NONE | 1 | ← HIGH RATE MONOCULAR CAPSULE |
| (t5,t5) | HIGHER THAN STANDARD VALUE | STANDARD VALUE | NONE | 1 | ← LOW RATE MONOCULAR CAPSULE |
| (t11,t12) | STANDARD VALUE | STANDARD VALUE | NONE | 2 | ← STANDARD BINOCULAR CAPSULE |
| (t13,t14) | STANDARD VALUE | HIGHER THAN STANDARD VALUE | NONE | 2 | ← HIGH ILLUMINATION BINOCULAR CAPSULE |
| (t15,t16) | HIGHER THAN STANDARD VALUE | STANDARD VALUE | NONE | 2 | ← LOW RATE BINOCULAR CAPSULE |
| (t17,t18) | STANDARD VALUE | STANDARD VALUE | YES | 2 | ← COMPRESSION BINOCULAR CAPSULE |

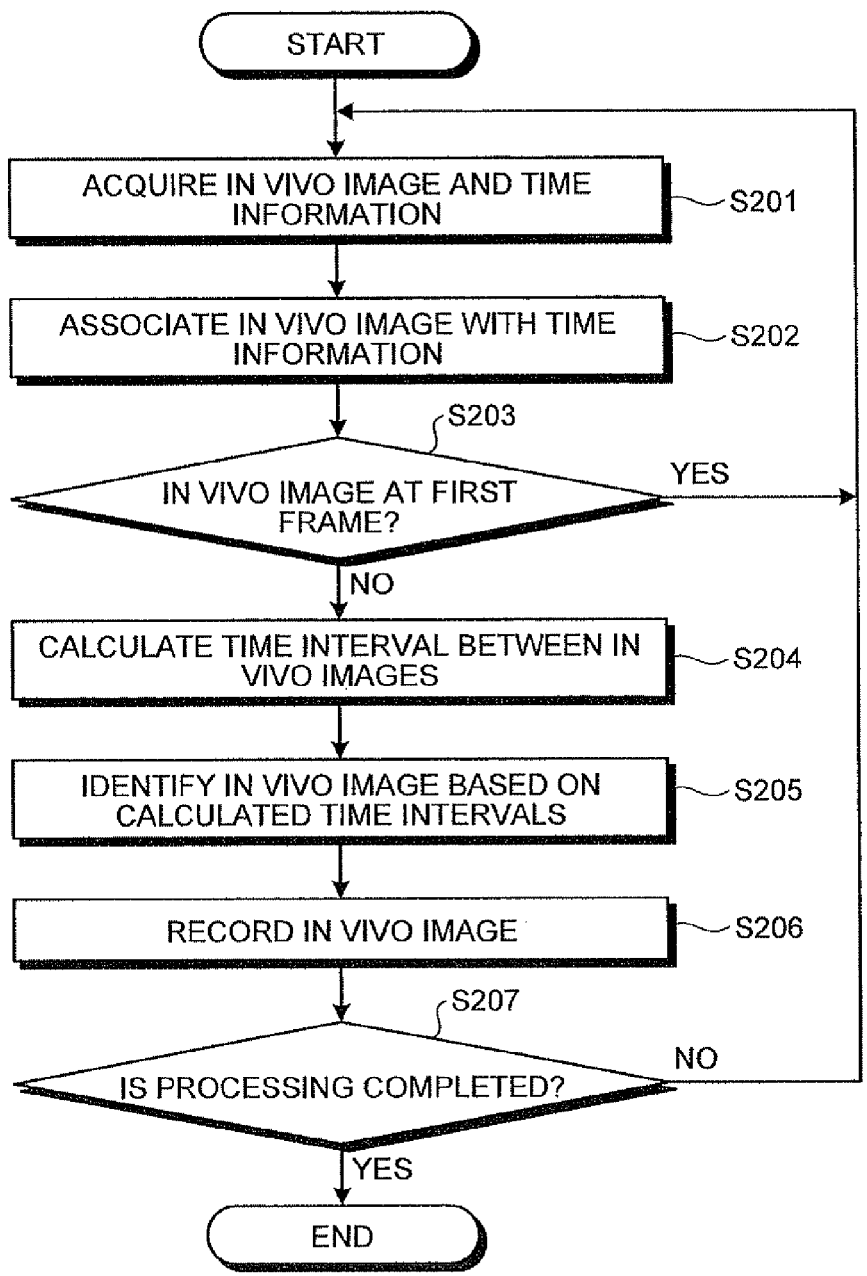

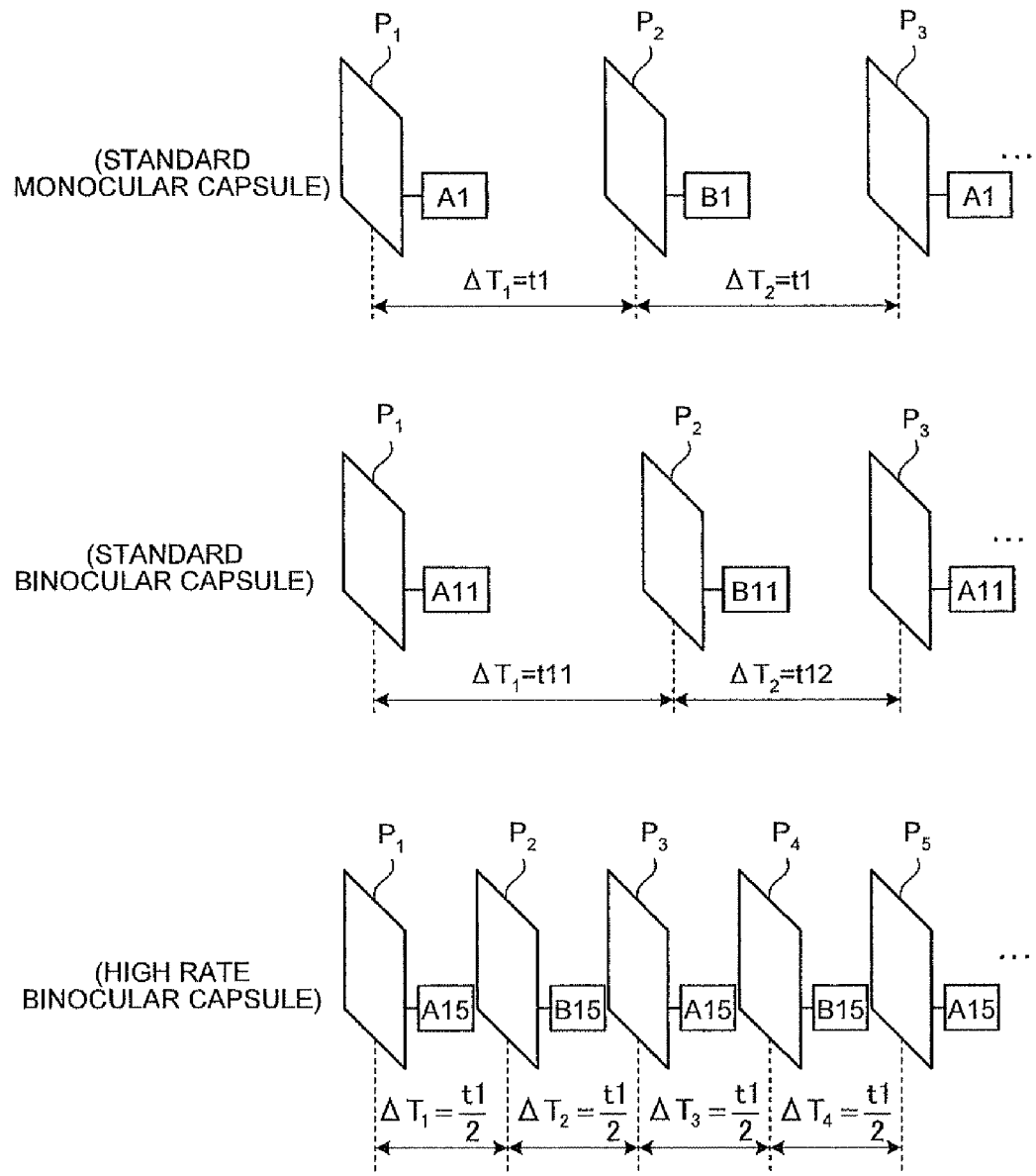

IN-VIVO IMAGE ACQUIRING APPARATUS, RECEIVING APPARATUS AND IN-VIVO IMAGE ACQUIRING SYSTEM

CROSS-REFERENCE TO RELATED APPLICATIONS

This application is based upon and claims the benefit of priority from Japanese Patent Application No. 2007-156741, filed Jun. 13, 2007, the entire contents of which are incorporated herein by reference.

BACKGROUND OF THE INVENTION

1. Field of the Invention

The present invention relates to an in-vivo image acquiring apparatus which is introduced into the internal body of a patient for acquiring an image of the internal body, a receiving apparatus and an in-vivo image acquiring system.

2. Description of the Related Art

In recent years, in the field of endoscope, a capsule endoscope equipped with an imaging function and radio communication function inside of its capsule type casing has appeared as an in-vivo image acquiring apparatus for acquiring an image in the body. The capsule endoscope is swallowed through a mouth of the patient for observation (examination) and after that, moved by peristaltic motion and the like inside the internal organ such as the stomach and the small intestine in a period until it is naturally excreted from the body under examination in order to take images in the internal organ of the subject (hereinafter, sometimes referred to as in-vivo image) successively at a predetermined time interval. The capsule endoscope transmits the in-vivo image taken (acquired) in this way successively to outside by radio.

The in-vivo image transmitted by such a capsule endoscope by radio is received by a receiving apparatus carried by this subject successively. This receiving apparatus includes a recording medium mounted detachably thereon and records a series of the in-vivo images received from the capsule endoscope inside the subject. After that, the recording medium which records the series of the in-vivo images of this subject is removed from this receiving apparatus and mounted to an image display unit. The image display unit acquires the series of the in-vivo images of the subject through this recording medium and displays the series of the in-vivo images of the subject on a display. In an in-vivo image acquiring system provided with the capsule endoscope, receiving apparatus and image display unit, a user such as medical doctor or nurse displays the series of the in-vivo images taken by the capsule endoscope on the image display unit to observe (examine) the inside of the organ of the subject through such a series of the in-vivo images (see, for example, Japanese Patent Application Laid-Open No. 2003-19111).

On the other hand, some type of a system for transmitting/receiving plural image data includes a data transmitting unit for transmitting image data supplied with identification information different for each frame rate and a data receiving unit for receiving image data of plural frame rates corresponding to such identification information and transmits image data of plural frame rates to a plurality of terminals (see, for example, Japanese Patent Application Laid-Open No. 11-112569).

The function of the aforementioned capsule endoscope is classified to plural types depending on a difference in the number of frames of the in-vivo images taken per unit time and a difference in the number of held imaging units for imaging a series of the in-vivo images. Such a capsule endoscope has unique identification information allocated preliminarily, attaches the identification information to a taken in-vivo image and transmits the in-vivo image supplied with such identification information to the receiving apparatus by radio. In this case, the receiving apparatus receives the identification information unique to the capsule endoscope together with the in-vivo images, identifies the in-vivo images depending on each function of the capsule endoscope specified by this identification information and records the in-vivo images of this subject in the recording medium. The image display unit acquires the in-vivo images identified depending on each function of the capsule endoscope through the recording medium and displays the images of the acquired in-vivo images by classifying by each function of the capsule endoscope (for example, by each imaging unit of the capsule endoscope). As a result, the in-vivo images of the subject are displayed in a display style which allows a medical doctor or nurse to observe easily.

SUMMARY OF THE INVENTION

An in-vivo image acquiring apparatus according to an aspect of the present invention includes an imaging unit for taking in-vivo images of a subject; a transmitting unit for transmitting each in-vivo image taken by the imaging unit to outside by radio; and a control unit for controlling the transmitting unit to transmit the in-vivo images successively by radio at a time interval depending on function or feature of the in-vivo image acquiring apparatus.

A receiving apparatus according to another aspect of the present invention includes a receiving unit for receiving in-vivo images of a subject, the in-vivo images being transmitted by radio by an in-vivo image acquiring apparatus for taking the in-vivo images with at least one imaging unit; a detecting unit for detecting time information concerning a time when the in-vivo image is received or a time relating to the receiving time; and a control unit for calculating a time interval between continuous in-vivo images of the in-vivo images based on the time information detected by the detecting unit and identifying a type of the in-vivo image acquiring apparatus based on the calculated time interval.

An in-vivo image acquiring system according to still another aspect of the present invention includes an in-vivo image acquiring apparatus which is introduced into an inside of a subject to take in-vivo images of the subject and transmits the in-vivo images of the subject successively by radio at a time interval depending on function or feature of the in-vivo image acquiring apparatus; and a receiving apparatus which receives the in-vivo image transmitted successively by radio by the in-vivo image acquiring apparatus, detects each time information which specifies the received in-vivo image, calculates the time interval which is a difference of the time information between continuous in-vivo images of the in-vivo images, and identifies the in-vivo images depending on a type of the in-vivo image acquiring apparatus based on the calculated time interval.

The above and other objects, features, advantages and technical and industrial significance of this Invention will be better understood by reading the following detailed description of presently preferred embodiments of the invention, when considered in connection with the accompanying drawings.

BRIEF DESCRIPTION OF THE DRAWINGS

FIG. 19 is an example of a data table in which a correspondence between combinations of the time intervals of respective in-vivo images and the function of the capsule endoscope;

FIG. 21 is a flow chart exemplifying the processing procedure which the control unit of the receiving apparatus of the fourth embodiment of the present invention performs; and FIG. 22 is a schematic view for explaining an operation of the identification processor which identifies the in-vivo images depending on each function unique to the capsule endoscope based on a combination of the time intervals of the respective in-vivo images.

DETAILED DESCRIPTION OF THE PREFERRED EMBODIMENTS

Hereinafter, the preferred embodiments of the in-vivo image acquiring apparatus, the receiving apparatus and the in-vivo image acquiring system of the present invention will be described with reference to the accompanying drawings. In the meantime, the present invention is not limited to the embodiments described in this specification.

Figure 1:
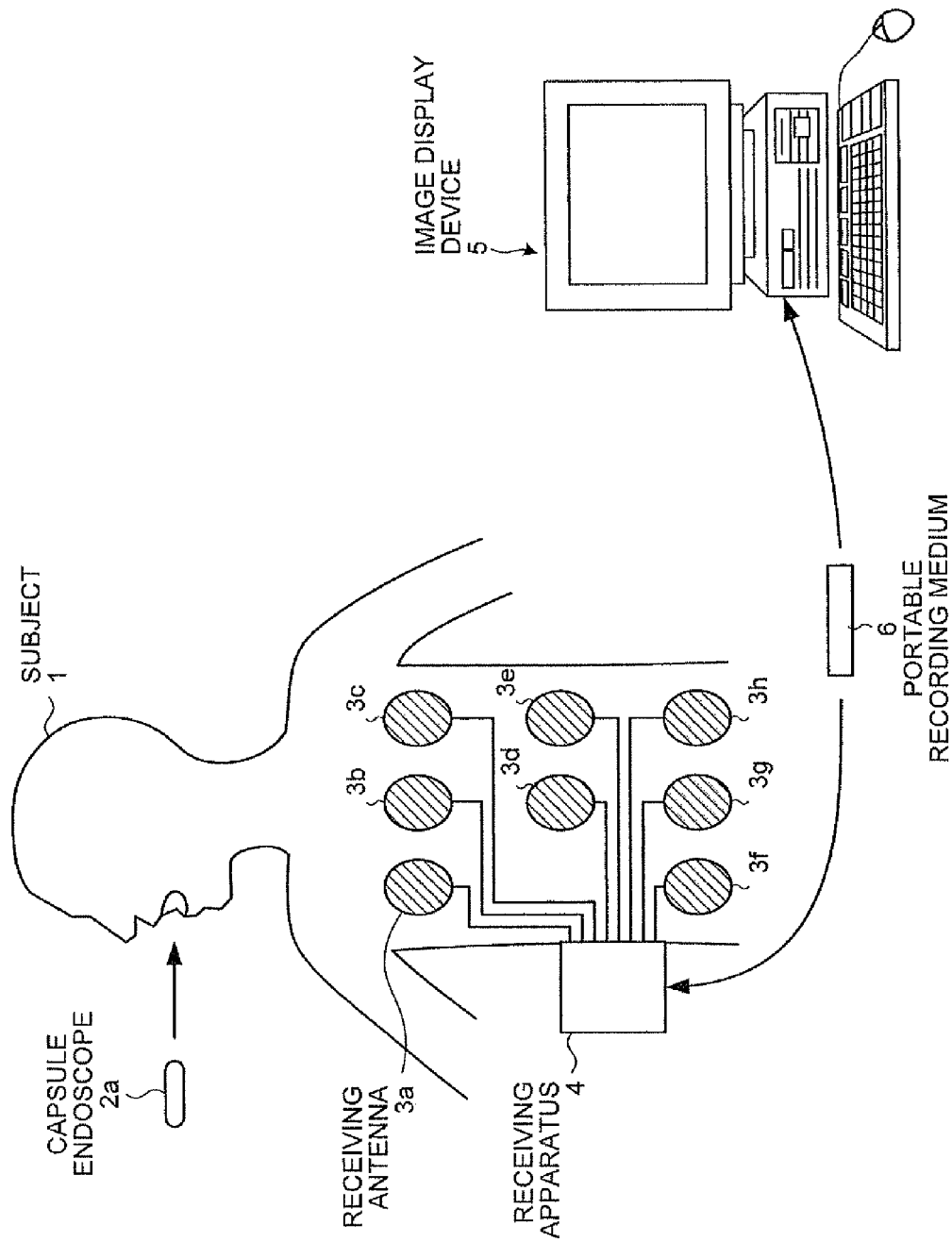
FIG. 1 is a schematic view showing an example of the configuration of an in-vivo image acquiring system according to a first embodiment of the present invention.

FIG. 1 is a schematic view showing an example of the configuration of the in-vivo image acquiring system according to a first embodiment of the present invention. As shown in FIG. 1, the in-vivo image acquiring system of the first embodiment includes a capsule endoscope 2a which is an example of the in-vivo image acquiring apparatus for imaging a series of in-vivo images of a subject 1, a receiving apparatus 4 for receiving the series of the in-vivo images of the subject 1 from the capsule endoscope 2a introduced into the inside of the subject 1, an image display device 5 for displaying the series of the in-vivo images (in other words, a series of in-vivo images taken by the capsule endoscope 2a) of the subject 1 received by the receiving unit 4 and a portable recording medium 6 for use in transfer of data between the receiving apparatus 4 and the image display device 5.

The capsule endoscope 2a functions as an in-vivo image acquiring apparatus which is introduced into the inside of the subject 1 for imaging the in-vivo images of the subject 1. More specifically, the capsule endoscope 2a is swallowed through a mouth of the subject 1 and after that, is moved inside of the internal organ of the subject 1 by peristaltic motion and the like in order to take the in-vivo images of the subject 1. Each time the capsule endoscope 2a takes an in-vivo image of the subject 1, it transmits an image signal containing the taken in-vivo image to the receiving apparatus 4 successively by radio. In this case, the capsule endoscope 2a transmits each in-vivo image of the subject 1 successively by radio at a time interval corresponding to the function unique to the endoscope 2a.

In the meantime, the functions unique to the capsule type capsule endoscope 2a are classified depending on for example, the number of held imaging units for imaging an in-vivo image of the subject 1, an amount of illumination of an illuminating unit for illuminating the inside of the internal organ (image pickup field) of the subject 1, the number of frames of the in-vivo images (imaging frames) taken per unit time (for example, a second) and the like.

The receiving apparatus 4 receives the in-vivo images of the subject 1 taken by the capsule endoscope 2a and accumulates the received in-vivo images. More specifically, the receiving apparatus 4 has a plurality of receiving antennas 3a to 3h and is carried by the subject 1 the organ of which the capsule endoscope 2a is to be introduced into. The receiving apparatus 4 receives an image signal transmitted by the capsule endoscope 2a inside of the subject 1 by radio successively through the plural receiving antennas 3a to 3h so as to obtain the in-vivo images of the subject 1. The receiving apparatus 4 has a portable recording medium 6 which is mounted detachably and records the in-vivo images of the subject 1 acquired from the capsule endoscope 2a. In this case, the receiving apparatus 4 calculates a time interval between respective continuous in-vivo images of the acquired in-vivo images and identifies each in-vivo image of the subject 1 depending on each function unique to the capsule endoscope 2a based on the calculated time interval. The receiving apparatus 4 records each in-vivo image of the subject 1 in the portable recording medium 6 such that it is identified depending on each function unique to the capsule endoscope capsule 2a.

The receiving antennas 3a to 3h are disposed dispersedly on the body surface of the subject along a traveling passage (that is, alimentary canal) of the capsule endoscope introduced into the inside of the organ of the subject and connected to the receiving apparatus 4. The receiving antennas 3a to 3h catch an image signal which the capsule endoscope 2a inside the subject 1 transmits successively by radio and transmit these caught image signals to the receiving apparatus 4 successively. In the meantime, the receiving antennas 3a to 3h may be disposed dispersedly on a jacket or the like which the subject 1 wears. One or more of the receiving antennas for catching such an image signal may be disposed on the subject 1 and the number is not limited to 8.

The image display device 5 has a structure like a work station for acquiring various kinds of data such as the in-vivo image of the subject 1 through the portable recording medium 6 and displaying this acquired various data on a display. More specifically, the portable recording medium 6 in which the in-vivo images are recorded is mounted detachably to the image display device 5 and the in-vivo images of the subject are taken in from the mounted portable recording medium 6. In this case, the image display device 5 acquires the in-vivo images identified depending on the function unique to the capsule endoscope 2a through the aforementioned receiving apparatus 4. The image display device 5 maintains and controls the acquired in-vivo images depending on each function unique to the capsule endoscope 2a and displays each in-vivo image in a style classified depending on each function unique to the capsule endoscope capsule 2a. Because the image display device 5 displays each in-vivo image of the subject 1 which is classified, a medical doctor or nurse can observe (examine) each in-vivo image of the subject 1 easily and effectively. In the meantime, user diagnoses the subject 1 by observing each in-vivo image of the subject 1 displayed by the image display device 5.

The portable recording medium 6 is a recording medium which can be carried and used for transfer of data between the receiving apparatus 4 and the image display device 5. More specifically, the portable recording medium 6 is mounted detachably to the receiving apparatus 4 and the image display device 5 and when it is mounted to either of the units, data can be output or recorded. When the portable recording medium 6 is mounted on the receiving apparatus 4, the in-vivo images of the subject 1 which the receiving apparatus 4 receives from the capsule endoscope capsule endoscope 2a is recorded and when the portable recording medium 6 is mounted on the image display device 5, recording data such as the in-vivo images of the subject 1 is transmitted to the image display device 5.

The various kinds of data which the portable recording medium 6 records are for example, the in-vivo images of the subject 1, time information (imaging time, reception time and the like) of each in-vivo image in the in-vivo images, patient information of the subject 1, examination information of the subject 1 and the like. Here, the patient information of the subject 1 is specific information for specifying the subject 1, such as a patient name of the subject 1, patient ID, birth date, sex, age and the like. The examination information of the subject 1 is specifying information for specifying a capsule endoscope examination (examination for observing the inside of the organ by introducing the capsule endoscope 2 into the inside of the organ) to be executed to the subject 1, and is, for example, examination ID and examination date.

Figure 2:
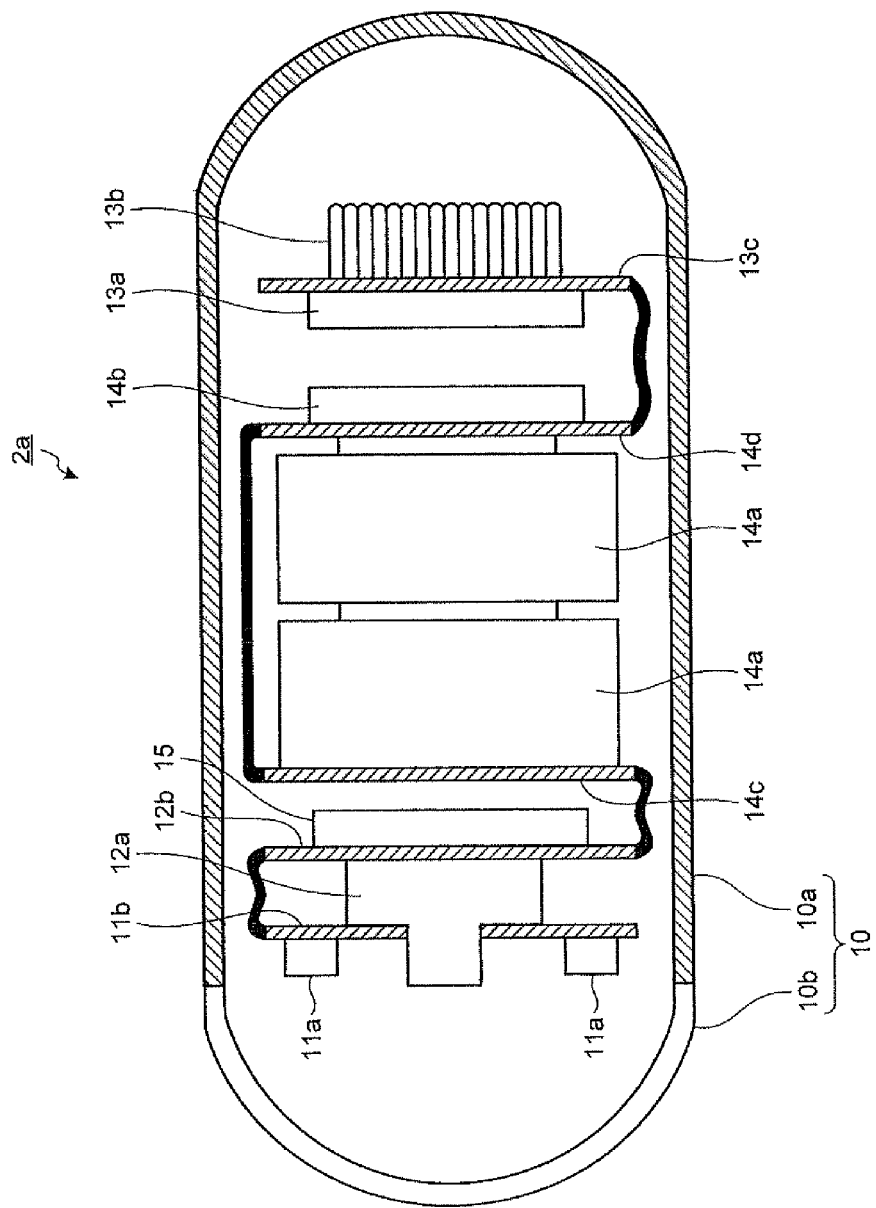
FIG. 2 is a schematic sectional view showing an example of the configuration of a capsule endoscope according to the first embodiment of the present invention.

Next, the structure of the capsule endoscope capsule endoscope 2a of the first embodiment of the present invention will be described. FIG. 2 is a schematic sectional view showing an example of the configuration of the capsule endoscope capsule endoscope 2a of the first embodiment of the present invention. As shown in FIG. 2, the capsule endoscope capsule endoscope 2a includes, in a capsule type casing 10, plural illuminating units 11a for illuminating the inside of the subject 1, an imaging unit 12a for imaging an image (in-vivo image) of the inside of the organ of the subject 1 illuminated by the illuminating units 11a, a radio unit 13a for transmitting an in-vivo image taken by the imaging unit 12a to the outside (aforementioned receiving apparatus 4) by radio and an antenna 13b. The capsule endoscope 2a includes a plurality of the illuminating unit 11a, the imaging unit 12a, a control unit 15 for controlling the radio unit 13a, a battery 14a for supplying electricity to each component (a plurality of the illuminating units 11a, imaging unit 12a, radio unit 13a and control unit 15) and a power source circuit 14b.

The casing 10 is a capsule type casing formed into a size which allows itself to be introduced into the inside of the subject 1 easily and formed of a casing main body 10a and an optical dome 10b. The casing main body 10a is a casing member having a cylindrical structure one end of which is open while the other end thereof is closed into a dome. The optical dome 10b is a transparent optical member formed into a dome and attached to the casing main body 10a such that it closes an opening end which is an end of the casing main body 10a. The casing 10 formed of the casing main body 10a and the optical dome 10b incorporates the respective components (illuminating unit 11a, imaging unit 12a, radio unit 13a, antenna 13b, battery 14a, power source circuit 14b, control unit 15 and the like) in a liquid-tight condition.

The plurality of the illuminating units 11a are realized using a light emission device such as LED and are disposed in the vicinity of the optical dome 10b inside the casing 10 such that they are mounted on an illumination substrate 11b which is a substantially disk-shaped rigid circuit substrate. The plurality of the illuminating units 11a emit illumination light of a predetermined light intensity so as to illuminate the inside of the organ of the subject 1 (speaking in detail, image pickup field by the imaging unit 12a) through the optical dome 10b.

The imaging unit 12a is disposed inside the casing 10 such that it is mounted on an image pickup substrate 12b which is a rigid circuit substrate formed substantially in a disk shape so as to take an image of an object illuminated by the plurality of the illuminating units 11a. More specifically, the imaging unit 12a is constituted of a solid image pickup element such as CCD or CMOS image sensor and an optical system for forming an image of the object on the light receiving surface of this solid image pickup element and opposes the optical dome 10b such that the lens frame of this optical system is inserted in an opening portion of the illumination substrate 11b. Such an imaging unit 1a takes images of the inside of the organ (that is, in-vivo images of the subject 1) of the subject 1 illuminated by the plurality of the illuminating units 11a through the optical dome 10b at a predetermined imaging frame rate.

The radio unit 13a and the antenna 13b transmit each in-vivo image of the subject 1 taken successively by the imaging unit 12a to outside successively by radio. More specifically, the radio unit 13a and the antenna 13b are disposed inside the casing 10 such that they are mounted on a radio substrate 13c which is a rigid circuit substrate formed substantially in a disc shape. The radio unit 13a receives an image signal containing the in-vivo image of the subject 1 taken by the imaging unit 12a, and modulates the received image signal so as to generate radio signal containing the in-vivo image of the subject 1. The antenna 13b transmits radio signal generated by the radio unit 13a to the receiving apparatus 4 outside. In this case, the radio unit 13a transmits the in-vivo images of the subject 1 successively at a transmitting time interval (hereinafter referred to as transmitting-interval) corresponding to the function unique to the capsule endoscope capsule endoscope 2a under a control of the control unit 15. The in-vivo image of the subject 1 transmitted by radio is received by the receiving apparatus 4 through the above-described receiving antennas 3a to 3h.

The battery 14a and the power source circuit 14b function as an incorporated power source for supplying electricity to respective components (the plurality of the illuminating units 11a, imaging unit 12a, radio unit 13a, and control unit 15) of the capsule endoscope 2a. More specifically, the two batteries 14a are for example, a button type battery such as silver oxide battery and are electrically connected to power source substrates 14c, 14d such that they are sandwiched by the power source substrates 14, 14d as a pair which are rigid circuit substrates formed substantially in a disk shape. In the meantime, the number of the batteries 14a may be of any number as long as they can generate a drive power sufficient for the respective components of the capsule endoscope 2a and is not limited to two. On the other hand, the power source circuit 14b is installed on the power source substrate 14d so as to supply electricity of the battery 14a to the respective components of the capsule endoscope 2a through the power source substrates 14c, 14d. The power source substrate 14d is provided with a magnetic switch (not shown) for generating a control signal for turning ON/OFF supply of electricity by detecting an external magnetic force. The power source substrates 14c, 14d, the illumination substrate 11b, the image pickup substrate 12b, and the radio substrate 13c are connected electrically through a flexible circuit substrate.

The control unit 15 is disposed inside the casing 10 such that it is mounted on for example, the image pickup substrate 12b, functioning as a control means for controlling the plurality of the illuminating units 11a, the imaging unit 12a and the radio unit 13a. More specifically, the control unit 15 controls operation timings of the respective illuminating units 11a and the imaging unit 12a for the imaging unit 12a to take images of the inside of the organ of the subject 1 illuminated by the plurality of the illuminating units 11a and controls the illuminating units 11a and the imaging unit 12a so as to take the in-vivo images of the subject 1 successively at an imaging frame rate unique to the capsule endoscope 2a. The control unit 15 has various kinds of parameters concerning image processing such as white balance and has an image processing function for generating an image signal containing the in-vivo images of the subject 1 taken by the imaging unit 12a. The control unit 15 control the radio unit 13a so as to transmit such image signals to the radio unit successively 13a so that the signals are transmitted successively at a predetermined transmission frame rate by radio. In this case, the control unit 15 controls so as to transmit the in-vivo images of the subject 1 successively at a transmission interval corresponding to the function unique to the capsule endoscope 2a.

Figure 3:
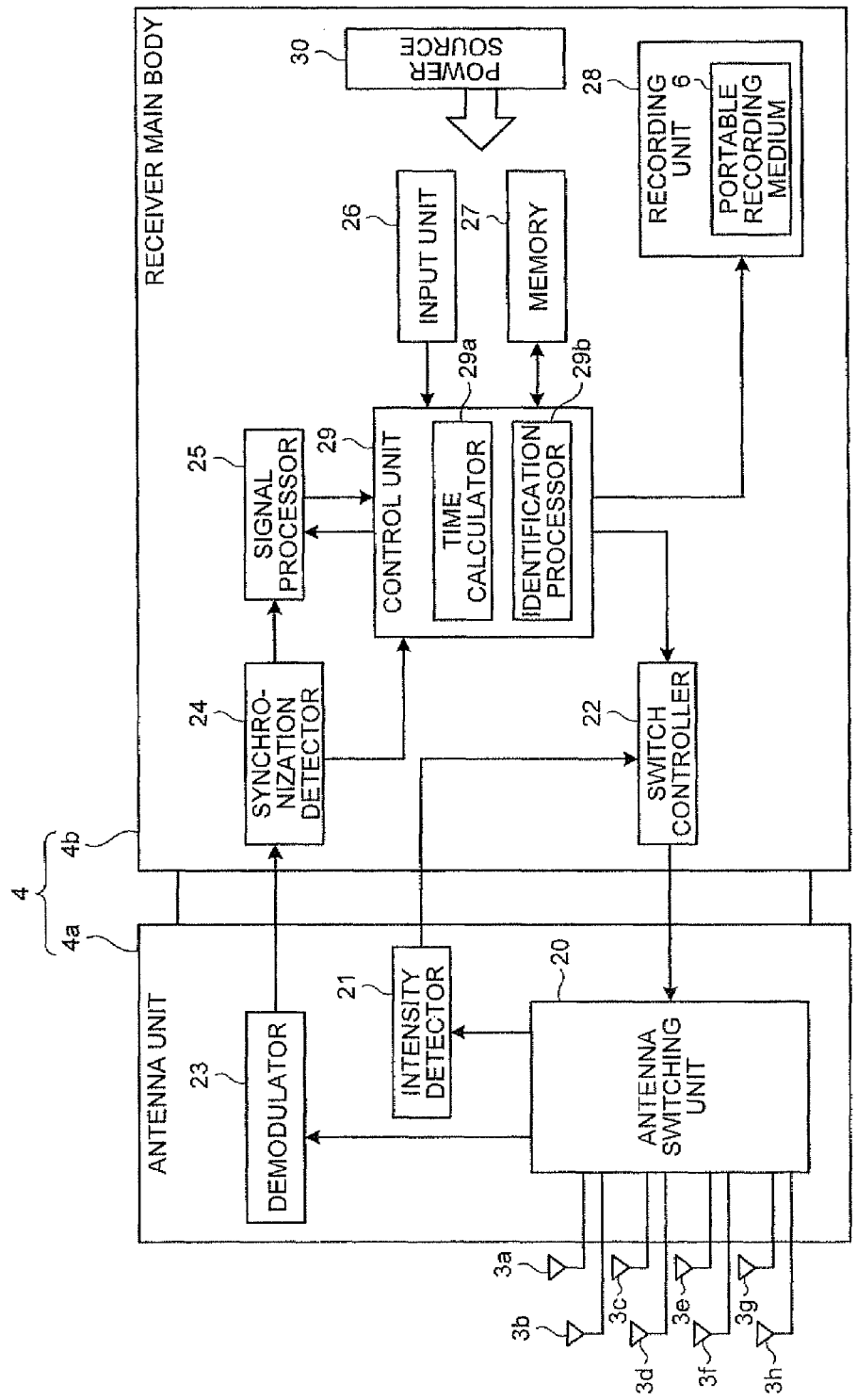
FIG. 3 is a block diagram showing schematically an example of the configuration of a receiving apparatus according to the first embodiment of the present invention.

Next, the configuration of the receiving apparatus 4 of the first embodiment of the present invention will be described. FIG. 3 is a block diagram showing schematically an example of the configuration of the receiving apparatus 4 according to the first embodiment of the present invention. As shown in FIG. 3, the receiving unit 4 of the first embodiment includes an antenna unit 4a and a receiver main body 4b.

The antenna unit 4a functions as a receiving means for receiving an image signal transmitted by the capsule endoscope 2a inside the subject 1 by radio. The receiver main body 4b acquires the in-vivo image of the subject 1 according to an image signal received through the antenna unit 4a and accumulates the acquired in-vivo images of the subject 1. The receiving apparatus 4 is realized by connecting the antenna unit 4a and the receiver main body 4b through a connector.

As shown in FIG. 3, the antenna unit 4a includes an antenna switching unit 21 to which the aforementioned receiving antennas 3a to 3h are connected, an intensity detector 21 for detecting the received electric intensity of a radio signal received through the receiving antennas 3a to 3h and a demodulator 23 for demodulating such radio signal to base band signal (image signal). On the other hand, the receiver main body 4b, as shown in FIG. 3, includes a switch controller 22 for controlling the antenna switch operation of an antenna switching unit 20, a synchronization detector 24 for detecting a synchronous signal contained in an image signal extracted by the demodulator 23 and a signal processor 25 for processing the image signal in a frame unit in which the synchronous signal is detected by the synchronization detector 24. Further, the receiver main body 4b includes an input unit 26, a memory 27, a recording unit 28 for recording the in-vivo images of the subject 1 in the portable recording medium 6, a control unit 29 for controlling the respective components of the receiving apparatus 4, a power source 30 for supplying electricity to the respective components of the receiving apparatus 4.

The antenna switching unit 20 has the receiving antennas 3a to 3h and performs antenna switch operation for switching connecting state between each of the receiving antennas 3a to 3h and the demodulator 23. If speaking in detail, the antenna switching unit 20 switches a receiving antenna to be connected to the demodulator 23 from the plural receiving antennas 3a to 3h based on a control of the switch controller 22 and transmits each received radio signal through the antennas 3a to 3h successively to the intensity detector 21. The antenna switching unit 20 executes antenna switch operation based on a control of the switch controller 22 so as to select a receiving antenna suitable for receiving the radio signal transmitted from the capsule endoscope 2a from the receiving antennas 3a to 3h, thereby connecting this selected receiving antenna (any one of the receiving antennas 3a to 3h) and the demodulator 23.

The intensity detector 21 detects the received electric field intensity of each radio signal received successively through the receiving antennas 3a to 3h. More specifically, the intensity detector 21 detects the received electric field intensity of each radio signal from the capsule endoscope 2a received successively through the receiving antennas 3a to 3h which are switched over in succession by the antenna switching unit 20. The intensity detector 21 transmits such a signal as received signal strength indicator (RSSI) as a detection result of the received electric field intensity to the switch controller 22.

The switch controller 22 controls the antenna switching unit 20 so as to switch connecting state between each of the plurality of the receiving antennas 3a to 3h and the demodulator 23 under a control of the control unit 29. The switch controller 22 selects a receiving antenna which allows the received electric field intensity of the radio signal to be the highest from the receiving antennas 3a to 3h based on a signal (such as RSSI signal) indicating a received electric intensity detected by the intensity detector 21 and controls the antenna switching unit 20 so as to connect this selected receiving antenna to the demodulator 23.

The demodulator 23 demodulates the radio signal from the capsule endoscope 2a received through the receiving antennas 3a to 3h to an image signal which is a base band signal. More specifically, the demodulator 23 demodulates a radio signal received through a receiving antenna (any one of the receiving antennas 3a to 3h) selected by the antenna switching unit 20 so as to extract an image signal from this radio signal. The image signal extracted by the demodulator 23 is a base band signal which contains at least an image data (in-vivo image of the subject 1) taken by the capsule endoscope 2a. The demodulator 23 transmits such an image signal to the synchronization detector 24.

The synchronization detector 24 acquires an image signal extracted by the demodulator 23 and detects a synchronous signal (vertical synchronous signal or horizontal synchronous signal) contained in the acquired image signal. Consequently, the synchronization detector 24 detects a head or an end of the image signals in the frame unit corresponding to the in-vivo image of a frame and transmits the image signals in the frame unit to the signal processor 25. The synchronization detector 24 counts a time using for example, crystal oscillator and each time it detects a head or an end of the image signals in the frame unit, that is, each time the synchronous signal contained in the image signal is detected, it detects time information of that detection time. The time information detected by the synchronization detector 24 is specifying information which specifies each of the in-vivo images of the subject 1 corresponding to each image signal in the frame unit. The synchronization detector 24 transmits such time information to the control unit 29 successively.

The signal processor 25 acquires the image signals in the frame unit from the synchronization detector 24 and performs a predetermined image processing on the acquired image signals in the frame unit each time so as to generate the in-vivo images (more specifically, in-vivo images of the subject 1 taken by the capsule endoscope 2a) in the frame unit corresponding to the image signals in the frame unit successively. The signal processor 25 transmits the generated in-vivo images of the subject 1 to the control unit 29 successively.

The input unit 26 is realized using an input key or an input button for input of information and inputs various kinds of instruction information to be instructed to the control unit 29 to the control unit 29 corresponding to an input operation by user. The memory 27 is realized using a memory device such as a RAM and stores therein the in-vivo image generated by the signal processor 25 and time information detected by the synchronization detector 24 temporarily in a period until the control unit 29 identifies the in-vivo image of the subject 1 depending on the function unique to the capsule endoscope 2a. Various kinds of information stored by the memory 27 are read out by the control unit 29 as required.

The recording unit 28 records the in-vivo images of the subject 1 received from the capsule endoscope 2a. More specifically, the portable recording medium 6 is mounted detachably to the recording unit 28 and the in-vivo images is recorded in the portable recording medium 6 under a control by the control unit 29.

The control unit 29 is constituted of a CPU for executing processing program, ROM in which the processing program is stored preliminarily and a RAM for storing therein arithmetic operation parameter and the like so as to control respective components of the receiving unit 4. For example, the control unit 29 controls information input by the input unit 26, information storage and information read out by the memory 27 and recording of the in-vivo images and the like by the recording unit 28. The control unit 29 controls the switch controller 22 based on instruction information input by the input unit 26 and controls the antenna switching unit 20 through a control by this switch controller 22. Consequently, the control unit 29 controls start and end of the reception of radio signal through the receiving antennas 3a to 3h. The control unit 29 controls the signal processor 25 so as to generate and output the in-vivo image specified by the time information acquired from the synchronization detector 24.

The control unit 29 has a time calculator 29a and an identification processor 29b and calculates a time interval corresponding to the function unique to the capsule endoscope 2a, that is, a transmission interval of each in-vivo image by the capsule endoscope 2a based on the time information of each in-vivo image acquired successively from the synchronization detector 24 and identifies the in-vivo image of the subject 1 depending on the functions unique to the capsule endoscope 2a based on an acquired time interval. The control unit 29 controls the recording unit 28 so as to record each in-vivo image of the subject 1 in the portable recording medium 6 such that it is identified depending on the functions unique to the capsule endoscope 2a.

The time interval calculator 29a calculates a time interval between respective in-vivo images continuous in the in-vivo images of the subject 1 based on the time information of each in-vivo image detected by the synchronization detector 24. The time interval between the in-vivo images calculated by the time calculator 29a is a transmission interval of the in-vivo image by the capsule endoscope 2a, that is, a time interval corresponding to the functions unique to the capsule endoscope 2a. The identification processor 29b identifies each in-vivo image (each in-vivo image of the subject 1) generated and output successively by the signal processor 25 based on the time interval calculated by the time calculator 29a, depending on the functions unique to the capsule endoscope 2a.

Figure 4:
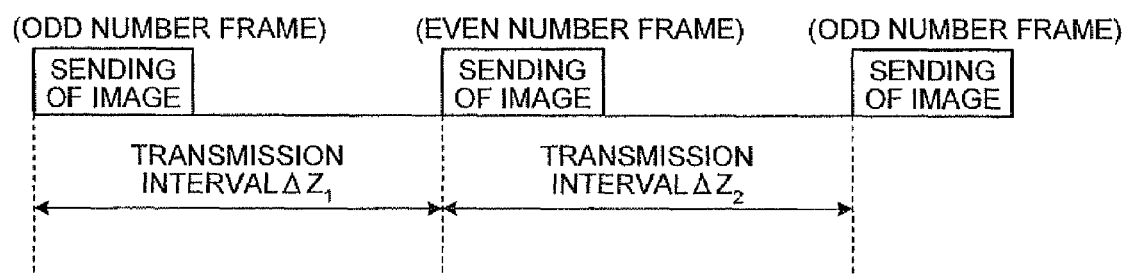
FIG. 4 is a schematic view exemplifying a transmission sequence of the capsule endoscope which transmits each in-vivo image of a subject successively by radio.

Next, the operation of the capsule endoscope 2a of the first embodiment of the present invention will be described. FIG. 4 is a schematic diagram exemplifying a transmission sequence of the monocular capsule endoscope 2a for transmitting the in-vivo images of the subject 1 successively. As shown in FIG. 4, the capsule endoscope 2a transmits the in-vivo images taken successively inside of the organ of the subject 1 according to transmission intervals $\Delta Z_1$, $\Delta Z_2$ corresponding to the functions unique to the capsule endoscope 2a.

More specifically, with the capsule endoscope 2a introduced into the organ of the subject 1, the control unit 15 makes the imaging unit 12a take the in-vivo images from a first frame to n frame (n is a positive integer) in succession and transmit the in-vivo images from the first frame to the n frame to the radio unit 13a successively. In this case, the control unit 15 controls the radio unit 13a to transmit the in-vivo images from the first frame to the second frame at the transmission interval $\Delta Z_1$ successively and then controls the radio unit 13a to transmit the in-vivo images at the second frame and third frame at the transmission interval $\Delta Z_2$ successively. The control unit 15 switches the transmission intervals $\Delta Z_1$, $\Delta Z_2$ depending on the in-vivo image like the case of the in-vivo images at the first frame to third frame successively and transmits the in-vivo images of the third frame and the following frames successively by radio. That is, as shown in FIG. 4, the control unit 15 makes the radio unit 13a transmit the in-vivo images at odd number frames taken successively by the imaging unit 12a and the in-vivo images at even number frames just after at the transmission interval $\Delta Z_1$ successively by radio and then makes the radio unit 13a transmit the in-vivo images at the even frames and the in-vivo images at the odd number frames just after at the transmission interval $\Delta Z_2$ successively by radio.

In the meantime, the transmission interval $\Delta Z_1$ may be a time interval from start of transmitting of the in-vivo image at the odd number frame by radio up to start of transmitting of the in-vivo image at the even number frame just thereafter by radio as shown in FIG. 4 or may be a time interval from end of transmitting of the in-vivo image of the odd number frame up to end of transmitting of the in-vivo image of the even number frame just thereafter by radio. Likewise, the transmission interval $\Delta Z_2$ may be a time interval from start of transmitting of the in-vivo image at the even number frame to start of transmitting of the in-vivo image at the odd number frame just thereafter or may be a time interval from end of transmitting of the in-vivo image of the even number frame to the end of transmitting of the in-vivo image at the odd number frame just thereafter.

A combination of the transmission intervals $\Delta Z_1$, $\Delta Z_2$ of the in-vivo images continuous in the frame number is a combination of the time intervals corresponding to the functions unique to the capsule endoscope 2a which acquires these in-vivo images and is uniquely set to this capsule endoscope 2a. That is, such a combination of the transmission intervals $\Delta Z_1$, $\Delta Z_2$ is time information which can specify the functions unique to the capsule endoscope 2a. As described above, the control unit 15 switches the transmission intervals $\Delta Z_1$, $\Delta Z_2$ successively depending on the in-vivo images and make the radio unit 13a transmit the in-vivo images from the first frame to the n frame successively by radio. As a result, the capsule endoscope 2a can transmit the in-vivo images of the subject 1 taken by the imaging unit 12a successively by radio and notify the receiving apparatus 4 of the functions unique to the capsule endoscope 2a depending on the combination of the transmission intervals $\Delta Z_1$, $\Delta Z_2$ of the respective in-vivo images.

In the meantime, the transmission frame rate of the radio unit 13a which transmits the in-vivo images of the subject 1 at the aforementioned transmission intervals $\Delta Z_1$, $\Delta Z_2$ successively by radio is 2 [frame/second] if the sum of the transmission intervals $\Delta Z_1$, $\Delta Z_2$ continuous as shown in FIG. 4 is a unit time (=1 second). On the other hand, the imaging frame rate of the imaging unit 12a for taking the in-vivo images of the subject 1 may be of the same value as this transmission frame rate or of a different value as long as it uniquely corresponds to the transmission frame rate of the radio unit 13a.

Figure 5:
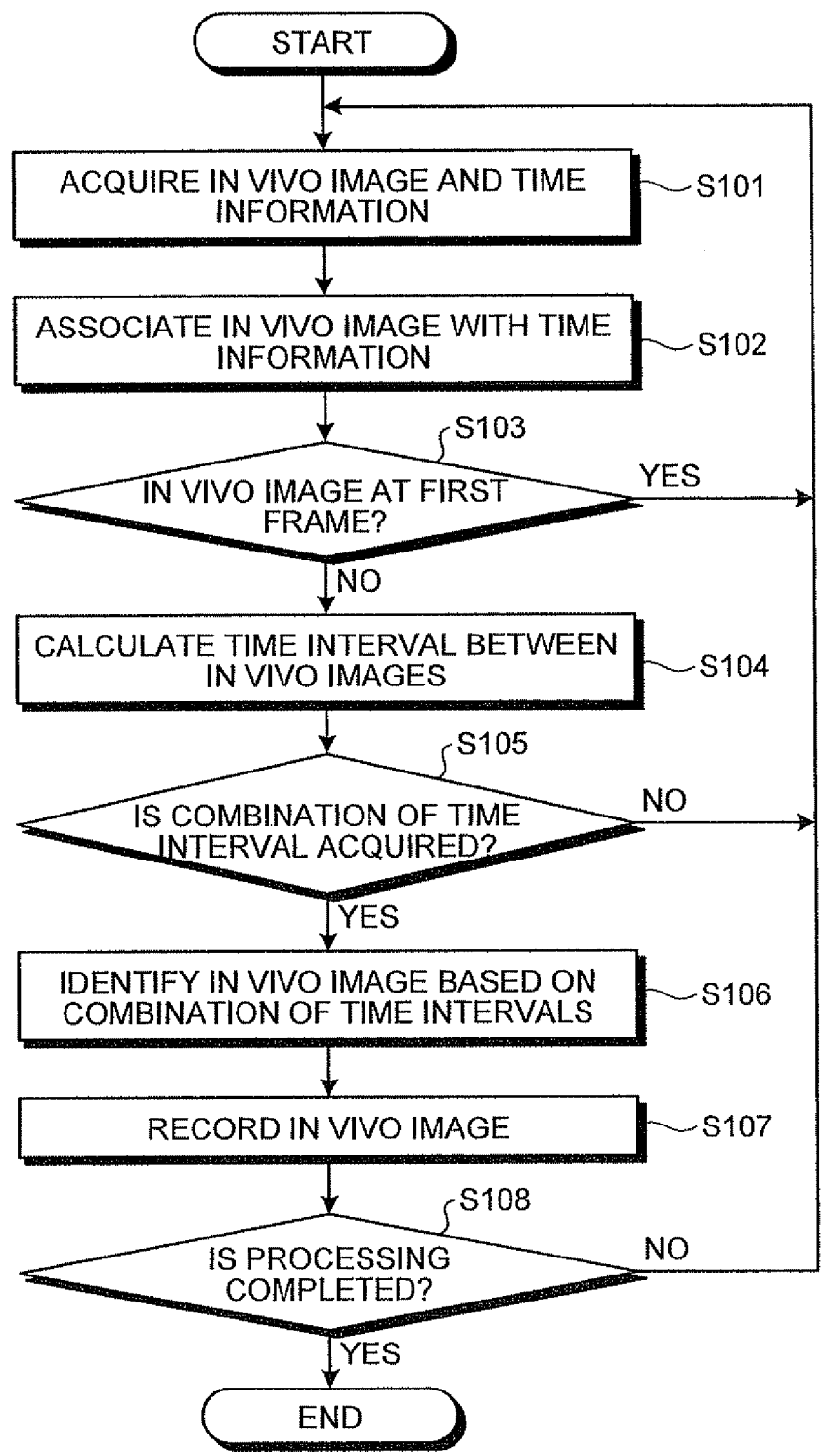
FIG. 5 is a flow chart exemplifying processing procedure which the control unit of the receiving apparatus of the first embodiment carries out.

Next the operation of the receiving apparatus 4 of the first embodiment of the present invention will be described. FIG. 5 is a flow chart exemplifying the procedure which the control unit 29 of the receiving apparatus 4 of the first embodiment of the present invention carries out. As described above, the receiving apparatus 4 receives the in-vivo images of the subject 1 transmitted by radio by the capsule endoscope 2a. The control unit 29 identifies the in-vivo images of the subject 1 received from the capsule endoscope 2a depending on the functions unique to the capsule endoscope 2a and records in the portable recording medium successively.

That is, as shown in FIG. 5, the control unit 29 acquires the in-vivo images of the subject 1 received from the capsule endoscope 2a and time information for specifying the in-vivo image (step S101). More specifically, the control unit 29 acquires time information (for example, detection time of the synchronous signal contained in the image signal) of the in-vivo image detected by the synchronization detector 24 and acquires the in-vivo image in the frame unit specified by this time information from the signal processor 25.

Next, the control unit 29 associates the in-vivo image acquired in step S101 with the time information (step S102). More specifically, the control unit 29 associates the time information acquired from the synchronization detector 24 with the in-vivo image acquired from the signal processor 25 so as to know the time information which specifies this in-vivo image. In this case, the control unit 29 stores the in-vivo image and time information associated in such a way in the memory 27 temporarily and maintains and manages the in-vivo images and time information so that they can be read out as required.

After that, the control unit 29 determines whether or not the in-vivo image associated with the time information in this step S102 is an in-vivo image at the first frame (step S103). In the receiving apparatus 4, initialization processing for initial setting as a receiving unit for acquiring the in-vivo image of this subject 1 is carried out before the in-vivo image of the subject 1 is received from the capsule endoscope 2a. The portable recording medium 6 mounted to the recording unit 28 of the receiving apparatus 4 is formatted by such initialization processing so that it turns to a state in which no in-vivo image is recorded. The control unit 29 confirms the recording status of the portable recording medium 6 and if the in-vivo image of the subject 1 is not recorded in the portable recording medium 6, it determines that the aforementioned in-vivo image is an in-vivo image at the first frame (step S103: YES). In this case, the control unit 29 returns to the step S101, in which the procedure subsequent to this step S101 is repeated.

On the other hand, if the in-vivo image of the subject 1 is recorded in the portable recording medium 6 as a result of confirming the recording status of the portable recording medium 6, the control unit 29 determines that the aforementioned in-vivo image is not an in-vivo image at the first frame (in-vivo images subsequent to the second frame) (step S103: NO), and calculates a time interval between the continuous two in-vivo images (step S104). In this case, the time calculator 29a reads out time information $T_n$ of the newest in-vivo image (that is, in-vivo image having the largest frame number currently) acquired by the control unit 29 currently and time information $T_{n-1}$ of an in-vivo image just before continuous with the newest in-vivo image from the memory 27 and calculates a time interval $\Delta T_{n-1}$ which is a time difference between the time information $T_n$ and time information $T_{n-1}$. The time interval $\Delta T_{n-1}$ calculated by the time calculator 29a is a time interval between the respective in-vivo images continuous of the in-vivo images which the control unit 29 acquires successively from the signal processor 25 and corresponds to any one of the transmission intervals $\Delta Z_1$, $\Delta Z_2$ of the in-vivo images by the capsule endoscope 2a. The control unit 29 stores the time information $T_{n-1}$ calculated by the time calculator 29a temporarily in the memory 27.

After that, the control unit 29 determines whether or not any combination of the time interval between the continuous in-vivo images of the in-vivo image has been acquired (step S105) and if not (step S105: NO), the procedure returns to the step S105, in which the procedure subsequent to this step S101 is repeated. When the control unit 29 repeats the procedure of steps S101 to S105, the time calculator 29a calculates the time intervals $\Delta T_{n-2}$, $\Delta T_{n-1}$ between the respective in-vivo images continuous of the in-vivo images acquired in succession from the signal processor 25, successively. As a result, the control unit 29 acquires the combination of the time intervals $\Delta T_{n-2}$, $\Delta T_{n-1}$.

In the meantime, the time interval $\Delta T_{n-2}$ is a time interval between the in-vivo images $P_{n-2}$ and $P_{n-1}$ on a head side of three in-vivo images $P_{n-2}$, $P_{n-1}$, $P_n$ continuous in frame number and the time interval $\Delta T_{n-1}$ is a time interval between the in-vivo images $P_{n-1}$ and $P_n$ on an end side thereof. A combination of the two continuous time intervals $\Delta T_{n-2}$, $\Delta T_{n-1}$ corresponds to a combination of transmission intervals $\Delta Z_1$, $\Delta Z_2$ corresponding to the function unique to the capsule endoscope 2a.

When the control unit 29 acquires the combination of the time intervals $\Delta T_{n-2}$, $\Delta T_{n-1}$ of the in-vivo images (step S105: YES), it identifies these in-vivo images based on the acquired combination of the time intervals $\Delta T_{n-2}$, $\Delta T_{n-1}$ (step S106). In this case, the identification processor 29b reads out the time intervals $\Delta T_{n-2}$, $\Delta T_{n-1}$ stored temporarily in the memory 27 and identifies each in-vivo image based on the combination of the time intervals $\Delta T_{n-2}$, $\Delta T_{n-1}$ read out in this way. Here, the combination of the time intervals $\Delta T_{n-2}$, $\Delta T_{n-1}$ corresponds to the combination of the transmission intervals $\Delta Z_1$, $\Delta Z_2$ corresponding to the function unique to the capsule endoscope 2a. Therefore, the identification processor 29b can determined the function unique to the capsule endoscope 2a based on the combination of the time intervals $\Delta T_{n-2}$, $\Delta T_{n-1}$ and can identify each in-vivo image depending on each determined function. The identification processor 29b adds identification information corresponding to the function unique to the capsule endoscope 2a to the in-vivo images $P_{n-2}$, $P_{n-1}$, $P_n$ so that the in-vivo images $P_{n-2}$, $P_{n-1}$, $P_n$ are identified depending on the function unique to the capsule endoscope 2a.

After that, the control unit 29 controls the recording unit 28 so as to record each in-vivo image identified in the step S106 in the portable recording medium 6 (step S107). In this case, the identification processor 29b records each in-vivo image supplied with the identification information corresponding to the function unique to the capsule endoscope 2a in the portable recording medium 6 successively. Then, the control unit 29 determines whether or not processing of all the in-vivo images of the subject 1 is completed (step S108) and if not (step S108: NO), the procedure returns to the step S101, in which the procedure subsequent to this step slot is repeated. On the other hand, when an instruction information about termination of the processing is input by the input unit 26, the control unit 29 determines that the processing is completed (step S108: YES) and this processing is terminated.

Figure 6:
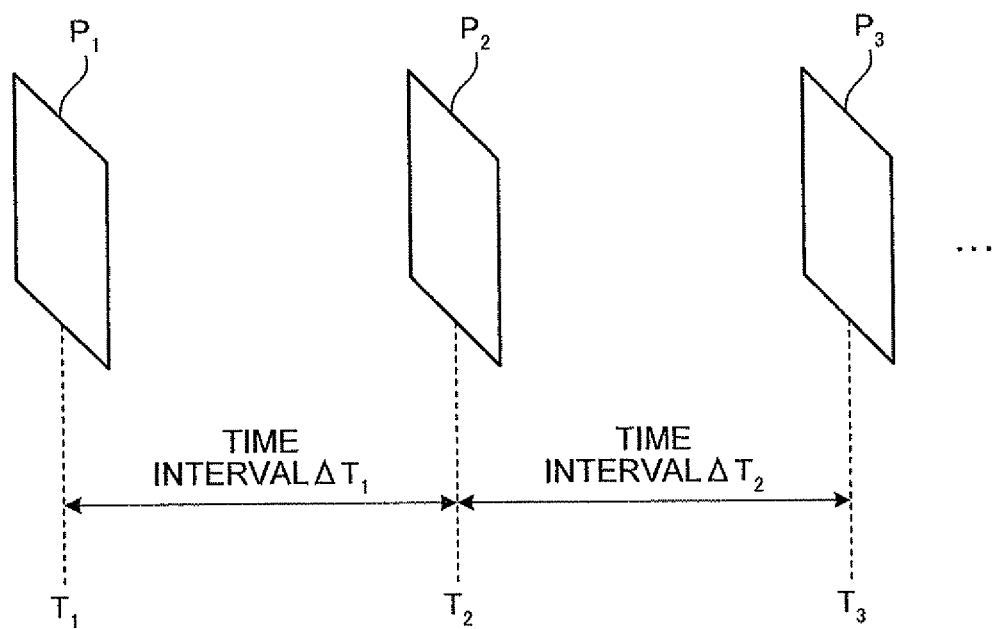
FIG. 6 is a schematic view exemplifying a time interval of respective in-vivo images calculated by a time calculator.
Figure 7:
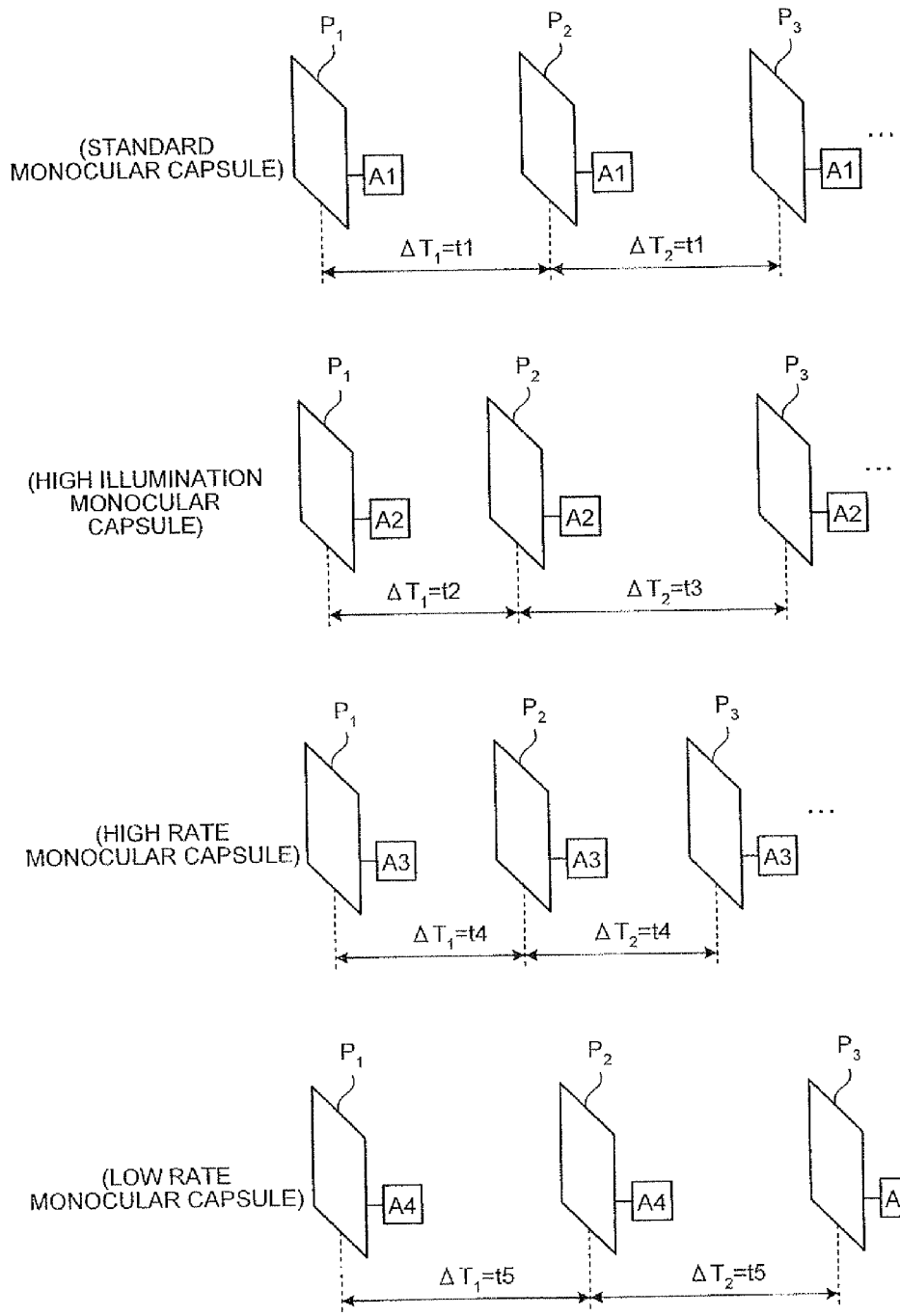
FIG. 7 is a schematic view for explaining an operation of the identification processor which identifies the in-vivo images depending on each function unique to the capsule endoscope based on a combination of the time intervals of the respective in-vivo images.

Next, the operation of the identification processor 29b for identifying each in-vivo image of the subject 1 depending on each function unique to the capsule endoscope 2a will be described by exemplifying the functions unique to the capsule endoscope 2a. FIG. 6 is a schematic view for exemplifying the time interval between the in-vivo images calculated by the time calculator 29a. FIG. 7 is a schematic diagram for explaining the operation of the identification processor 29b for identifying each in-vivo image depending on each function unique to the capsule endoscope based on any combination of the time intervals of the in-vivo images.

When the capsule endoscope 2a inside the subject 1 transmits the in-vivo images from the first frame to the third frame successively at the transmission intervals $\Delta Z_1$, $\Delta Z_2$ (see FIG. 4) by radio as described above, the receiving apparatus 4 receives the in-vivo images from the first frame to the third frame. In this case, the control unit 29 of the receiving apparatus 4 acquires time information $T_1$, $T_2$, $T_3$ from the synchronization detector 24 successively so that it acquires in-vivo image $P_1$ at the first frame, in-vivo image $P_2$ at the second frame and in-vivo image $P_3$ at the third frame from the signal processor 25. As described above, the control unit 29 associates the time information $T_1$ with the in-vivo image $P_1$, the time information $T_2$ with the in-vivo image $P_2$ and the time information $T_3$ with the in-vivo image $P_3$. In the meantime, the time information $T_1$ is specifying information of the in-vivo image $P_1$, the time information $T_2$ is specifying information of the in-vivo image $P_2$ and the time information $T_3$ is specifying information of the in-vivo image $P_3$.

As shown in FIG. 6, the time calculator 29a calculates a time difference between the time information $T_2$ of the in-vivo image $P_2$ and the time information $T_1$ of the in-vivo image $P_1$ as a time interval $\Delta T_1$ between the in-vivo images $P_1$ and $P_2$ and calculates a time difference between the time information $T_3$ of the in-vivo image $P_3$ and the time information $T_2$ of the in-vivo image $P_2$ as a time interval $\Delta T_2$ between the in-vivo images $P_2$ and $P_3$. The identification processor 29b identifies the in-vivo images $P_1$, $P_2$, $P_3$ of the subject 1 depending on the function unique to the capsule endoscope 2a based on the combination of the time intervals $\Delta T_1$, $\Delta T_2$ calculated by the time calculator 29a. In the meantime, the combination of the time intervals $\Delta T_1$, $\Delta T_2$ corresponds to the transmission intervals $\Delta Z_1$, $\Delta Z_2$ corresponding to the function unique to the capsule endoscope 2a.

As the types of the capsule endoscope 2a depending on the functions, for example, standard monocular capsule, high illumination monocular capsule, high rate monocular capsule and low rate monocular capsule are exemplified. In the meantime, the standard monocular capsule is a capsule endoscope which has a single imaging unit (for example, imaging unit 12a shown in FIG. 2) for taking the in-vivo images of the subject 1 and takes the in-vivo images of the subject 1 successively at a standard imaging frame rate (for example, 2 [frame/second]) by illuminating the inside of the organ of the subject 1 with standard illumination light intensity. The high illumination monocular capsule is a capsule endoscope which illuminates the inside of the organ of the subject 1 with higher illumination light intensity than the standard monocular capsule and has the same function as the standard monocular capsule as other function (the number of possessed imaging units and imaging frame rate). Such high illumination monocular capsule is suitable for the capsule endoscope which takes images inside the organ forming a large space like the stomach.

The high rate monocular capsule is a capsule endoscope which takes the in-vivo images of the subject 1 at a higher speed imaging frame rate than the standard monocular capsule and has the same function as the standard monocular capsule as other function (the number of possessed imaging units and illumination light intensity). Such high rate monocular capsule is suitable for a capsule endoscope for taking the images of the inside of the organ through which it passes in a short time, such as the esophagus. The low rate monocular capsule is a capsule endoscope which takes the in-vivo images of the subject 1 successively at a lower speed imaging frame rate than the standard monocular capsule and has the same function as the standard monocular capsule as other function (the number of possessed imaging units and illumination light intensity). Such a low rate monocular capsule is suitable for the capsule endoscope which takes the images of the inside of the organ which it takes a long time to pass through such as the small intestine and the large intestine.

In case where the capsule endoscope 2a is a standard monocular capsule, the capsule endoscope 2a transmits the in-vivo images $P_1$, $P_2$ at, for example, a transmission interval $\Delta Z_1$=t1 [second] successively by radio and then, transmits the in-vivo images $P_2$, $P_3$ at a transmission interval $\Delta Z_2$=t1 [second] successively by radio. In this case, the time calculator 29a calculates the time interval $\Delta T_1$=t1 of the in-vivo images $P_1$, $P_2$ and the time interval $\Delta T_2$=t1 of the in-vivo images $P_2$, $P_3$ successively.

As shown in FIG. 7, the identification processor 29b determines that the function unique to the capsule endoscope 2a is the function of the standard monocular capsule based on a combination (t1, t1) of the time intervals $\Delta T_1$, $\Delta T_2$ calculated by the time calculator 29a and then, adds identification information A1 indicating an in-vivo image corresponding to this determined function (standard monocular capsule) to the in-vivo images $P_1$, $P_2$, $P_3$. The identification processor 29b identifies the in-vivo images $P_1$, $P_2$, $P_3$ of the subject 1 depending on the functions unique to the standard monocular capsule.

On the other hand, if the capsule endoscope 2a is a high illumination monocular capsule, the capsule endoscope 2a transmits the in-vivo images $P_1$, $P_2$ at a transmission interval $\Delta Z_1$=t2 [second] for example, successively by radio and then transmits the in-vivo images $P_2$, $P_3$ at a transmission interval $\Delta Z_2$=t3 [second] successively by radio. In this case, the time calculator 29a calculates the time interval $\Delta T_1$=t2 of the in-vivo images $P_1$, $P_2$ and the time interval $\Delta T_2$=t3 of the in-vivo images $P_2$, $P_3$ successively. In the meantime, if a sum (t1+t2) of the transmission intervals $\Delta Z_1$, $\Delta Z_2$ of the aforementioned high illumination monocular capsule is a unit time, a sum (t2+t3) of the transmission intervals $\Delta Z_1$, $\Delta Z_2$ of the high illumination monocular capsule is of substantially the same value as the sum (t1+t1) of the transmission intervals $\Delta Z_1$, $\Delta Z_2$ of the standard monocular capsule.

As shown in FIG. 7, the identification processor 29b determines that the function unique to the capsule endoscope 2a is the function of the high illumination monocular capsule based on a combination (t2, t3) of the time intervals $\Delta T_1$, $\Delta T_2$ calculated by the time calculator 29a and then, adds identification information A2 indicating an in-vivo image corresponding to this determined function (high illumination monocular capsule) to the in-vivo images $P_1$, $P_2$, $P_3$. The identification processor 29b identifies the in-vivo images $P_1$, $P_2$, $P_3$ of the subject 1 depending on the functions unique to the standard monocular capsule.

On the other hand, if the capsule endoscope 2a is a high rate monocular capsule, the capsule endoscope 2a transmits the in-vivo images $P_1$, $P_2$ at a transmission interval $\Delta Z_1$=t4 [second] for example, successively by radio and then transmits the in-vivo images $P_2$, $P_3$ at a transmission interval $\Delta Z_2$=t4 [second] successively by radio. In this case, the time calculator 29a calculates the time interval $\Delta T_1$=t4 of the in-vivo images $P_1$, $P_2$ and the time interval $\Delta T_2$=t4 of the in-vivo images $P_2$, $P_3$ successively. In the meantime, a sum (t4+t4) of the transmission intervals $\Delta Z_1$, $\Delta Z_2$ of the high rate monocular capsule is smaller than the sum $(t_1+t1)$ of the transmission intervals $\Delta Z_1$, $\Delta Z_2$ of the standard monocular capsule.

As shown in FIG. 7, the identification processor 29b determines that the function unique to the capsule endoscope 2a is the function of the high rate monocular capsule based on a combination (t4, t4) of the time intervals $\Delta T_1$, $\Delta T_2$ calculated by the time calculator 29a and then, adds identification information A3 indicating an in-vivo image corresponding to this determined function (high rate monocular capsule) to the in-vivo images $P_1$, $P_2$, $P_3$. The identification processor 29b identifies the in-vivo images $P_1$, $P_2$, $P_3$ of the subject 1 depending on the function unique to the high rate monocular capsule.

On the other hand, if the capsule endoscope 2a is a low rate monocular capsule, the capsule endoscope 2a transmits the in-vivo images $P_1$, $P_2$ at a transmission interval $\Delta Z_1$=t5 [second] for example, successively by radio and then transmits the in-vivo images $P_2$, $P_3$ at a transmission interval $\Delta Z_2$=t5 [second] successively by radio. In this case, the time calculator 29a calculates the time interval $\Delta T_1$=t5 of the in-vivo images $P_1$, $P_2$ and the time interval $\Delta T_2$=t5 of the in-vivo images $P_2$, $P_3$ successively. In the meantime, a sum (t5+t5) of the transmission intervals $\Delta Z_1$, $\Delta Z_2$ of the low rate monocular capsule is larger than the sum (t1+t1) of the transmission intervals $\Delta Z_1$, $\Delta Z_2$ of the standard monocular capsule.

As shown in FIG. 7, the identification processor 29b determines that the function unique to the capsule endoscope 2a is the function of the low rate monocular capsule based on a combination (t5, t5) of the time intervals $\Delta T_1$, $\Delta T_2$ calculated by the time calculator 29a and then, adds identification information A4 indicating an in-vivo image corresponding to this determined function (low rate monocular capsule) to the in-vivo images $P_1$, $P_2$, $P_3$. The identification processor 29b identifies the in-vivo images $P_1$, $P_2$, $P_3$ of the subject 1 depending on the function unique to the low rate monocular capsule.

In the meantime, the time calculator 29a calculates the time intervals $\Delta T_3, \ldots, \Delta T_{n-2}, \Delta T_{n-1}$ of the in-vivo images subsequent to the third frame like the above-described $\Delta T_1$, $\Delta T_2$ successively. The identification processor 29b identifies the in-vivo images $P_3, \ldots, P_{n-1}, P_n$ subsequent to the third frame depending on the function unique to the capsule endoscope 2a based on the combination of the time intervals $(\Delta T_3, \Delta T_4), \ldots, (\Delta T_{n-2}, \Delta T_{n-1})$ calculated by the time calculator 29a successively like the in-vivo images $P_1$, $P_2$, $P_3$ from the first frame to the third frame.

Figure 8:
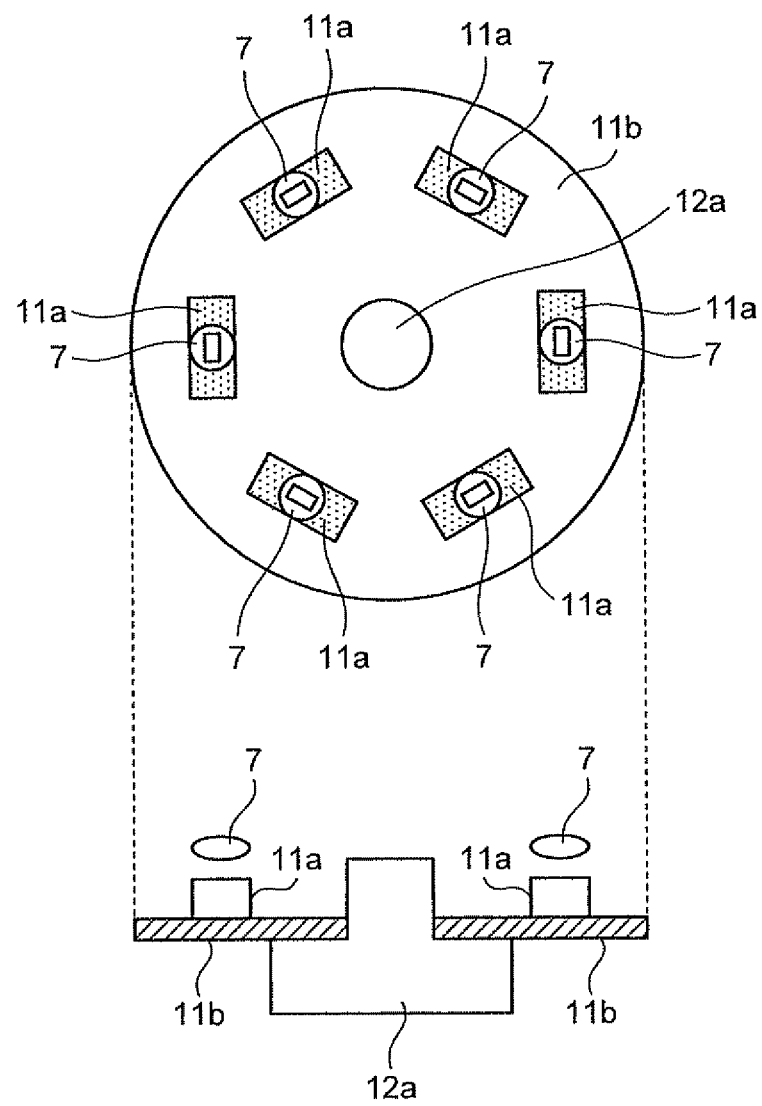
FIG. 8 is a schematic view showing an example of an illuminating mechanism of a high illumination monocular capsule.
Figure 9:
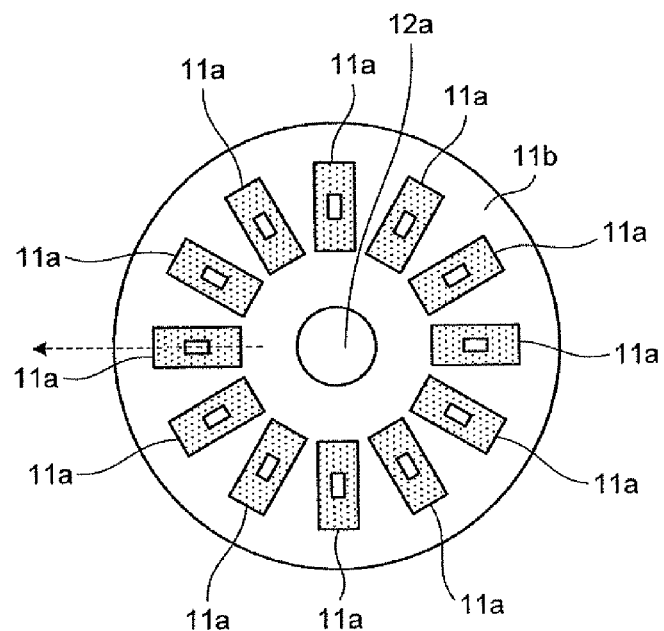
FIG. 9 is a schematic view showing a first modification of an illuminating mechanism of a high illumination monocular capsule.
Figure 10:
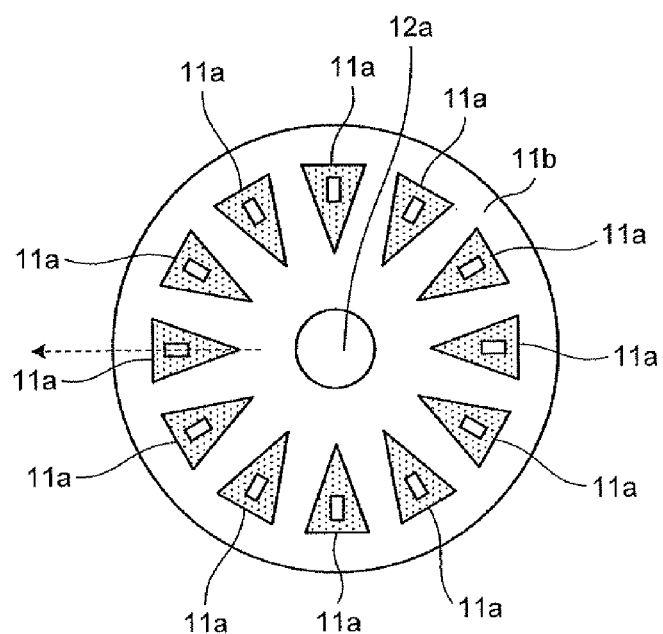
FIG. 10 is a schematic view showing a second modification of an illuminating mechanism of a high illumination monocular capsule.
Figure 11:
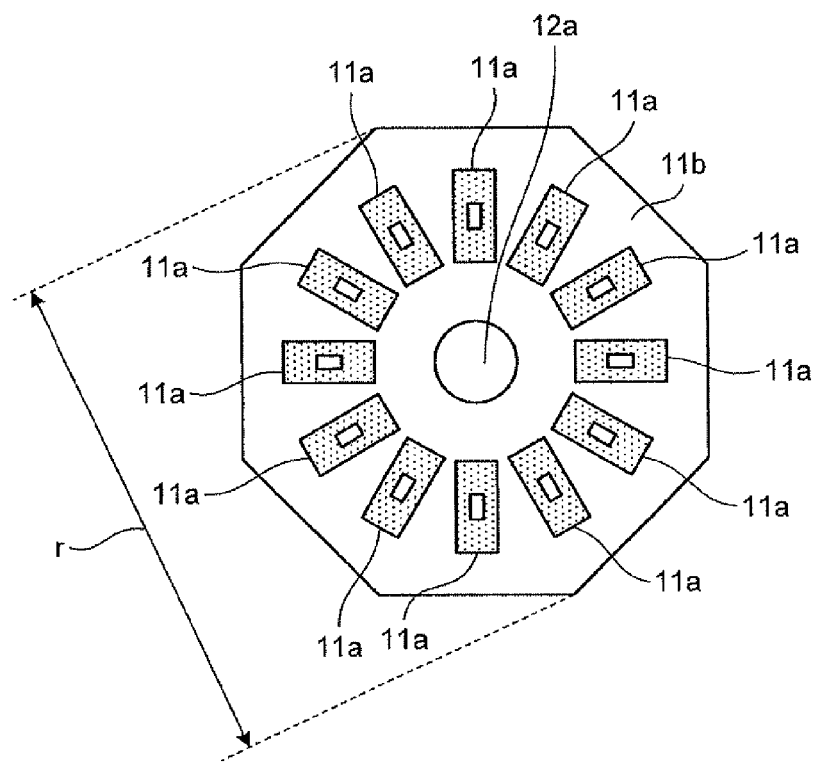
FIG. 11 is a schematic view showing a third modification of an illuminating mechanism of a high illumination monocular capsule.
Figure 12:
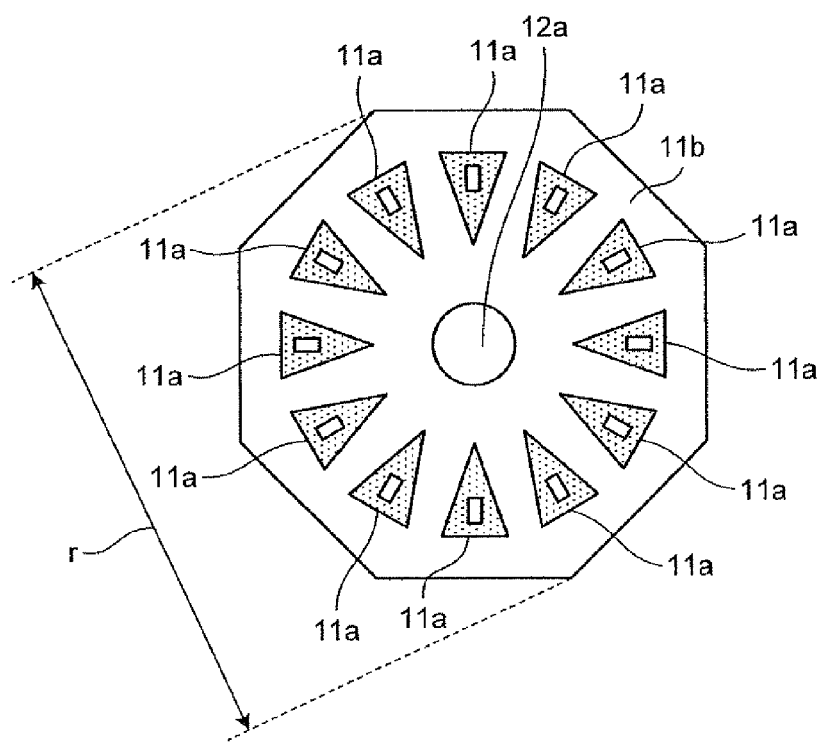
FIG. 12 is a schematic view showing a fourth modification of an illuminating mechanism of a high illumination monocular capsule.

Next, the illuminating mechanism of the capsule endoscope 2a in case where it functions as the high illumination monocular capsule will be described. FIG. 8 is a schematic view showing an example of an illuminating mechanism of the high illumination monocular capsule. FIG. 9 is a schematic view showing a first modification of an illuminating mechanism of the high illumination monocular capsule. FIG. 10 is a schematic view showing a second modification of an illuminating mechanism of the high illumination monocular capsule. FIG. 11 is a schematic view showing a third modification of an illuminating mechanism of the high illumination monocular capsule. FIG. 12 is a schematic view showing a fourth modification of an illuminating mechanism of the high illumination monocular capsule.

In case where the capsule endoscope 2a is a high illumination monocular capsule whose illumination light intensity is increased as compared to the standard monocular capsule, the illumination light intensity may be increased by increasing electricity supplied to a plurality of the illuminating units 11a shown in FIG. 2. However, it is desirable to increase the illumination light intensity without an increase of power consumption. That is, the high illumination monocular capsule increases the illumination light intensity for illuminating the inside of the organ of the subject 1 by concentrating respective illumination lights emitted by the plurality of the illuminating units 11a to a predetermined range.

As shown in FIG. 8, the plurality of the illuminating units 11a possessed by the high illumination monocular capsule are installed on the illumination substrate 11b such that the length direction of the illuminating unit 11a substantially coincides the direction of a tangent line of the outer circumference of the illumination substrate 11b like the standard monocular capsule. A lens 7 for focusing the illumination light is disposed on the top (that is, emission range of the illumination light) of each of the plural illuminating units 11a. In the meantime, FIG. 8 indicates a front view and a side view of the illumination substrate 11b provided with the plural illuminating units 11a and the imaging unit 12a.

The lens 7 focuses each illumination light emitted by the plural illuminating units 11a into the image pickup field of the imaging unit 12a so as to increase the light intensity of the illumination light irradiated to the inside of the organ of the subject 1, which is inside the image pickup field of the imaging unit 12a. The plural illuminating units 11a can illuminate the inside of the organ of the subject 1 more brightly due to an action of the lens 7.

Although the capsule endoscope 2a as the high illumination monocular capsule increases the illumination light intensity to the inside of the organ of the subject 1 due to the action of focusing of the lights by each lens 7 by disposing the lens 7 on the top of each of the plural illuminating units 11a as described above, the present invention is not limited to this example but the illumination light intensity to the inside of the organ of the subject 1 may be increased by increasing the number of the illuminating units 11a to be installed on the illumination substrate 11b.

More specifically, as shown in FIG. 9, the plurality of the illuminating units 11a are installed on the illumination substrate lib such that the length direction (direction of a dotted line arrow shown in FIG. 9) of each illuminating unit ha substantially coincides the diameter direction of the illumination substrate 11b. A large number of the illuminating units 11a can be disposed on the illumination substrate 11b as compared with the standard monocular capsule by installing the plurality of the illuminating units 11a on the illumination substrate 11b, thereby the illumination light intensity to the inside of the organ of the subject 1 being increased.

It is permissible to form the outer shape of each illuminating unit 11a in a triangular shape and dispose a plurality of the illuminating units 11a each having such an outer shape on the illumination substrate 11b at a high density. More specifically, the plurality of the illuminating units 11a each having the triangular outer shape may be installed on the illumination substrate 11b such that the length direction (for example, direction of a dotted line arrow shown in FIG. 10) of each illuminating unit 11a substantially coincides the diameter direction of the illumination substrate 11b. In this case, the plurality of the illuminating units 11a are disposed such that a pointed portion of the triangular outer shape opposes the imaging unit 12a (more specifically, side face of the lens frame). Consequently, as compared with a case of disposing the plurality of the illuminating units 11a each having a rectangular outer shape radially on the illumination substrate 11b (see FIG. 9), the plurality of the illuminating units 11a may be disposed on the illumination substrate 11b at a high density, so that the illumination light intensity to the inside of the organ of the subject 1 can be increased and reduction in size of the illumination substrate 11b, further reduction in size of the capsule endoscope can be accelerated.

Further, the substrate shape of the illumination substrate 11b is not limited to the disk shape as shown in FIGS. 9 and 10 but may be polygonal. More specifically, the plurality of the illuminating units 11a may be disposed radially on the illumination substrate 11b having a polygonal (for example, octagonal) substrate shape as shown in FIG. 11. In this case, the length direction of each of the plural illumination substrates 11b substantially coincides the diameter direction (direction from the center of the illumination substrate 11b toward the outer circumference) of the illumination substrate 11b. Because the polygonal illumination substrate 11b is disposed inside the capsule shaped casing 10 (see FIG. 2), the outer shape dimension r shown in FIG. 11 is set smaller than the inside diameter of the casing 10. Thus, the polygonal illumination substrate 11b is easier to manufacture than the above-mentioned circular illumination substrate.

The plurality of the illuminating units 11a disposed on the polygonal illumination substrate 11b is not limited to the illuminating unit having the rectangular shape as shown in FIG. 11 and may be an illuminating unit having the triangular outer shape shown in FIG. 10. More specifically, it is permissible to dispose the plurality of the illuminating units 11a each having the triangular outer shape radially on the illumination substrate 11b having the polygonal substrate shape as shown in FIG. 12. In this case, the plurality of the illuminating units 11a are disposed such that the pointed portions of the outer shape oppose the imaging unit 12a (more specifically, side face of the lens frame). As a result, the operating effect (high density mounting of the illuminating unit 11a) by the illuminating mechanism shown in FIG. 10 and the operating effect (improvement in ease of manufacturing of the illumination substrate 11b) by the illuminating mechanism shown in FIG. 11 can be enjoyed.

According to the first embodiment of the present invention, as described above, when transmitting the in-vivo images of the subject taken by the imaging unit, the in-vivo images are transmitted successively by radio at a time interval corresponding to the function unique to the device classified depending on the number of possessed imaging units, the frame rate, illumination light intensity or the like. Thus, the function unique to the device can be notified outside by a combination of the time intervals of the in-vivo images transmitted successively by radio without adding the identification information corresponding to the function unique to the device to each image signal. As a result, the in-vivo image acquiring apparatus which can transmit the in-vivo image of the subject successively by radio and identify the in-vivo images depending on the function unique to the device without any increase in the amount of information when the in-vivo image is transmitted by radio.

Further, the in-vivo images of the subject transmitted successively by radio by the in-vivo image acquiring apparatus are received in succession, the received time information for specifying the in-vivo image is detected successively, the time interval of the in-vivo image is calculated based on the detected time information so as to acquire a combination of the time intervals corresponding to the function unique to the in-vivo image acquiring apparatus and the in-vivo image of the subject is identified based on the acquired combination of the time intervals. Thus, the in-vivo image of the subject can be identified depending on the function unique to the in-vivo image acquiring apparatus based on the combination of the time intervals of the in-vivo images received in succession without receiving the identification information indicating the function unique to the device from the in-vivo image acquiring apparatus. Consequently, the receiving apparatus which can receive the in-vivo images of the subject in succession and identify the in-vivo images of the subject depending on the function unique to the in-vivo image acquiring apparatus without an increase in the amount of information when the in-vivo image acquiring apparatus transmits the in-vivo image by radio can be achieved.

Further, the in-vivo image acquiring system which can acquire the in-vivo images which can be identified depending on the function unique to the in-vivo image acquiring apparatus without an increase of the amount of information when the in-vivo image of the subject is transmitted by radio can be achieved by providing the in-vivo image acquiring apparatus and the receiving apparatus.

According to the in-vivo image acquiring apparatus, the receiving apparatus and the in-vivo image acquiring system of the present invention, the amount of information when the in-vivo image of the subject is transmitted by radio can be reduced as much as possible, so that power consumption when the in-vivo image of the subject is transmitted by radio can be suppressed thereby accelerating reduction of power consumption in the in-vivo image acquiring apparatus. Further, the in-vivo images of the subject can be accumulated such that they are identified depending on the function unique to the in-vivo image acquiring apparatus and by taking in the accumulated in-vivo images into the image display unit, the in-vivo images can be displayed on the image display unit such that they are identified depending on the function unique to the in-vivo image acquiring apparatus. As a result, a medical doctor or nurse can observe (examine) the in-vivo image of the subject displayed on the image display unit easily and effectively.

Next, a second embodiment of the present invention will be described. Although according to the first embodiment, the in-vivo images are identified depending on the function unique to the monocular capsule endoscope 2a having a single imaging unit 12a, according to the second embodiment, the in-vivo images are identified depending on the function unique to the compound eye capsule endoscope having a plurality of the imaging units as the imaging means for imaging the in-vivo images. Hereinafter, the binocular capsule endoscope having two imaging units will be explained as an example of the compound eye in-vivo image acquiring apparatus.

Figure 13:
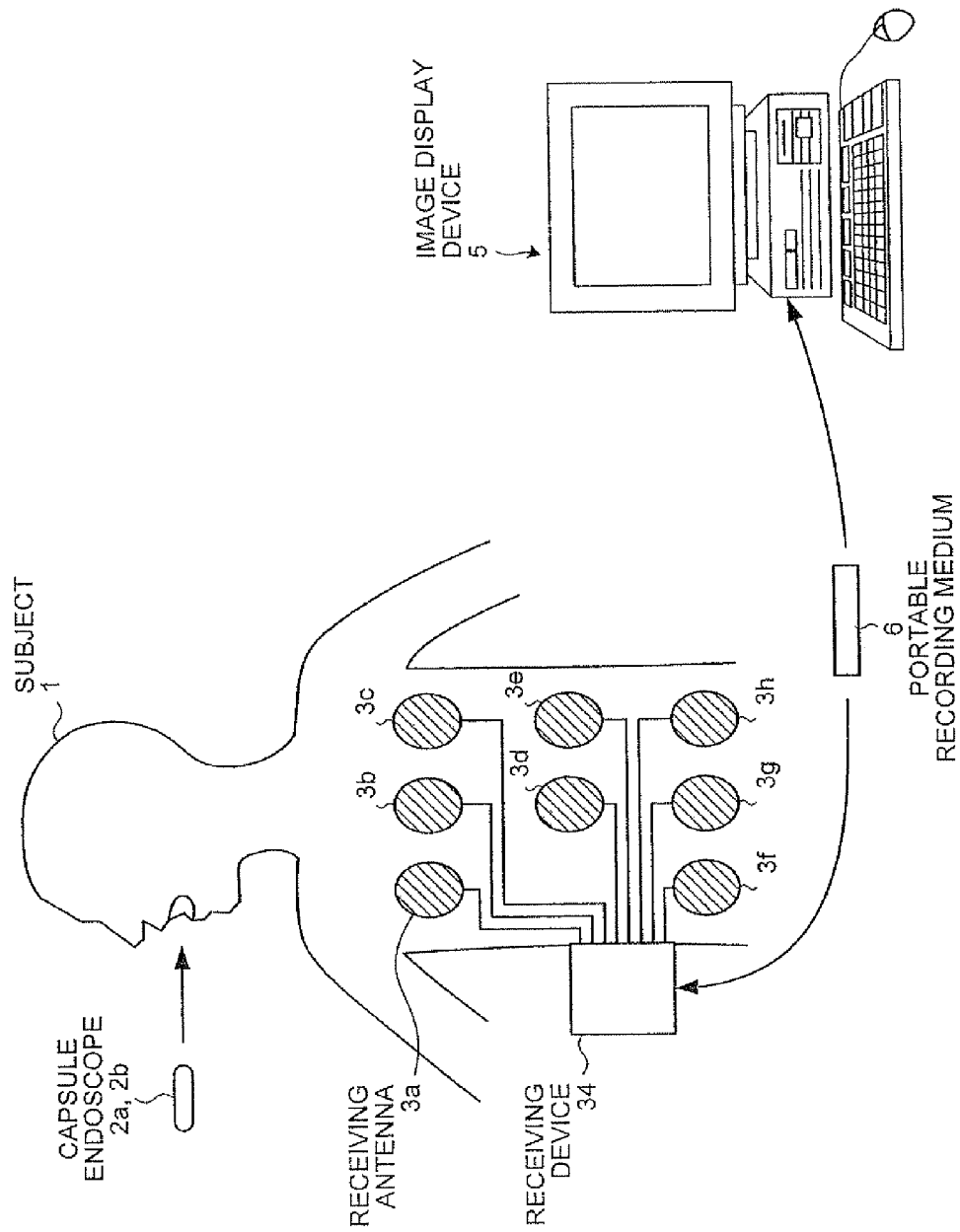
FIG. 13 is a schematic view showing an example of the configuration of the in-vivo image acquiring system according to a second embodiment of the present invention.

FIG. 13 is a schematic view showing an example of the configuration of the in-vivo image acquiring system according to the second embodiment of the present invention. As shown in FIG. 13, in the in-vivo image acquiring system of the second embodiment, as the type of the in-vivo image acquiring apparatus to be introduced into the subject 1, the binocular capsule endoscope 2b is added as well as the aforementioned monocular capsule endoscope 2a and a receiving apparatus 34 capable of identifying the in-vivo images depending on the function unique to the binocular capsule endoscope 2b as well as the monocular capsule endoscope 2a is possessed instead of the receiving apparatus 4. Other configuration is the same as the first embodiment and like reference numerals are attached to like components.

In the in-vivo image acquiring system of the second embodiment, the monocular capsule endoscope 2a or binocular capsule endoscope 2b is introduced into the inside of the organ of the subject 1 and the receiving apparatus 34 receives the in-vivo images taken by the monocular or binocular capsule endoscopes 2a, 2b introduced into the inside of the subject through the receiving antennas 3a to 3h. In this case, the receiving apparatus 34 identifies the in-vivo images depending on the function unique to the capsule endoscopes 2a, 2b.

Figure 14:
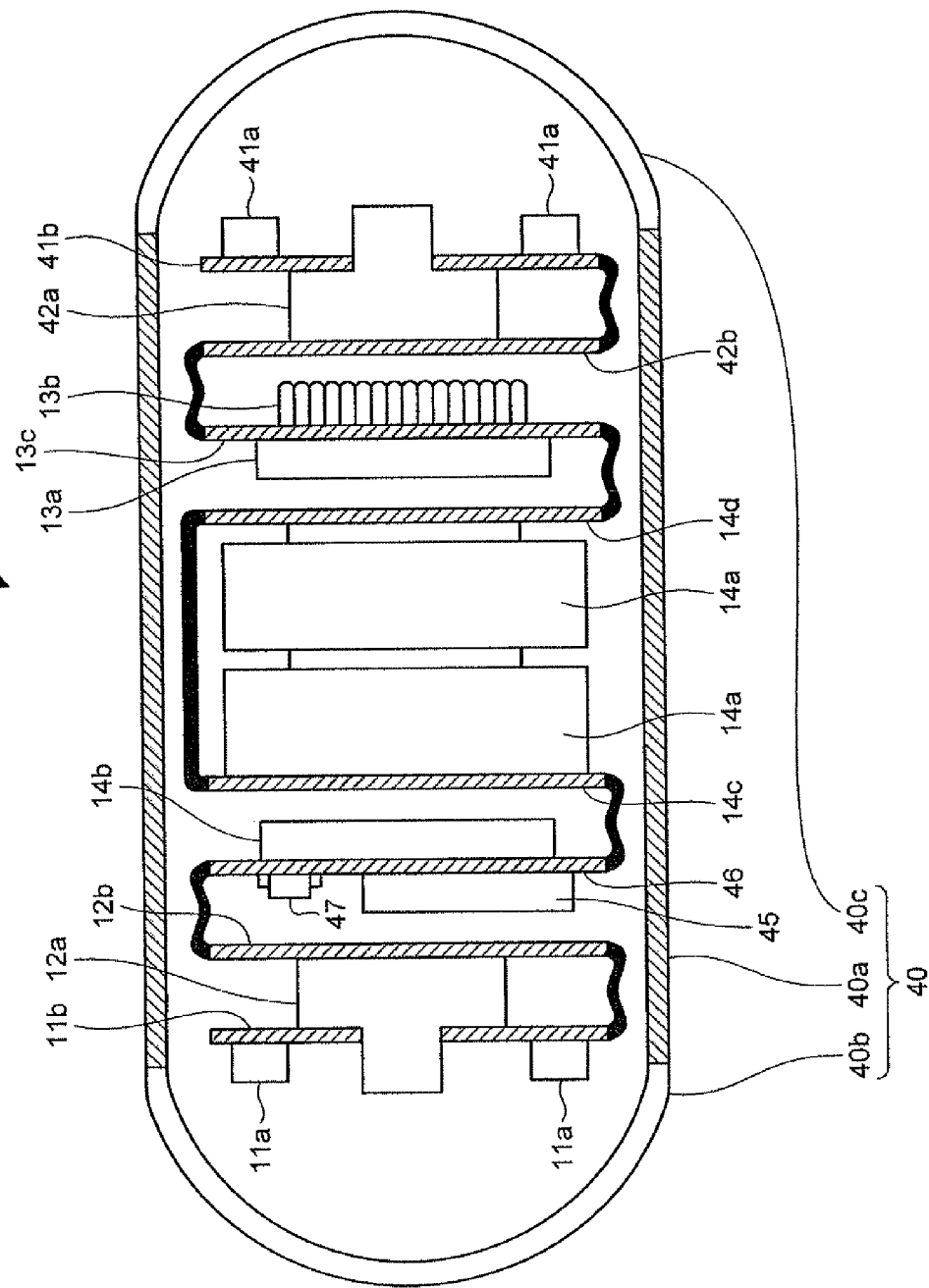
FIG. 14 is a schematic sectional view showing an example of the configuration of the capsule endoscope according to the second embodiment of the present invention.

Next, the configuration of the capsule endoscope 2b of the second embodiment of the present invention will be described. FIG. 14 is a schematic sectional view showing an example of the configuration of the capsule endoscope 2b according to the second embodiment of the present invention. The capsule endoscope 2b of the second embodiment is a binocular in-vivo image acquiring apparatus having two imaging units as described above and has substantially the same configuration by adding the imaging unit to the monocular capsule endoscope 2a. That is, as shown in FIG. 14, the capsule endoscope 2b has a casing 40 instead of the casing 10 of the capsule endoscope 2a of the first embodiment and has a control unit 45 instead of the control unit 15. The capsule endoscope 2b includes a plurality of illuminating units 41a mounted on the illumination substrate 41b and an imaging unit 42a mounted on the image pickup substrate 42b. Other configuration is the same as the first embodiment and like reference numerals are attached to like components.

The casing 40 is a capsule type casing formed into a size facilitating introduction thereof into the inside of the subject 1 like the casing 10 of the capsule endoscope 2a and formed of a casing main body 40a, and optical domes 40b, 40c. The casing main body 40a is a casing main body having a cylindrical structure whose both ends are open. The optical domes 40b, 40c are transparent optical members formed in a dome shape like the optical dome 10b of the capsule endoscope 2a and attached to the casing main body 40a so as to close the opening ends on both ends of the casing main body 40a. The casing 40 formed of the casing main body 40a and the optical domes 40b, 40c accommodates respective components (illuminating unit 11a, 41a, imaging unit 12a, 42a, radio unit 13a, antenna 13b, battery 14a, power source circuit 14b, control unit 45 and the like) in a liquid-tight condition.

The plurality of the illuminating units 41a are realized using a light emission device such as LED. The plurality of the illuminating units 41a are disposed in the vicinity of the optical dome 40c inside the casing 40 such that they are mounted on an illumination substrate 41b which is a substantially disk-shaped rigid circuit substrate. In this case, the plurality of the illuminating units 41a are installed on the illumination substrate 41b in substantially the same way as the illuminating units 11a on the illumination substrate 11b disposed on the optical dome 41b side. The plurality of the illuminating units 41a emit illumination light of a predetermined light intensity so as to illuminate the inside of the organ of the subject 1 (speaking in detail, image pickup field) through the optical dome 40c. On the other hand, the plurality of the illuminating units 11a illuminate the inside of the organ (if speaking in detail, the image pickup field of the imaging unit 12a) of the subject 1 through the optical dome 40b on an opposite side.

The imaging unit 42a is disposed inside the casing 40 such that it is mounted on an image pickup substrate 42b which is a rigid circuit substrate formed substantially in a disk shape, and has an image pickup field different from the above-mentioned imaging unit 12a. More specifically, the imaging unit 42a is constituted of a solid image pickup element such as CCD or CMOS image sensor and an optical system for forming an image of the object on the light receiving surface of this solid image pickup element and opposes the optical dome 40b such that the lens frame of this optical system is inserted in an opening portion of the illumination substrate 41b. Such an imaging unit 42a takes images of the inside of the organ (that is, in-vivo images of the subject 1) of the subject 1 illuminated by the plurality of the illuminating units 41a through the optical dome 40c at a predetermined imaging frame rate. On the other hand, the imaging unit 12a disposed on the optical dome 40b side takes images of the inside of the organ of the subject 1 illuminated by the plurality of the illuminating units 11a through the optical dome 40b at a predetermined imaging frame rate.

The control unit 45 is disposed inside the casing 40 such that it is installed on a control substrate 46 which is a rigid circuit substrate formed substantially in a disk shape and functions as a control means for controlling the plurality of the illuminating units 11a, 41a, the imaging units 12a, 42a and the radio unit 13a. More specifically, the control unit 45 controls the operation timings of the illuminating units 41a and the imaging unit 42a for the imaging unit 42a to take images of the inside of the organ of the subject 1 illuminated by the plurality of the illuminating units 41a and then controls the illuminating units 11a, 41a and the imaging units 12a, 42a so as to take the in-vivo images of the subject 1 successively with an imaging frame rate unique to the capsule endoscope 2b. In this case, the control unit 45 controls the illuminating units 11a, 41a and the imaging units 12a, 42a so as to take the in-vivo images of the subject 1 following a predetermined imaging order (for example, alternately) successively. The control unit 45 has an image processing function for generating an image signal containing the in-vivo image of the subject 1 taken by the imaging unit 42a. The control unit 45 controls the radio unit 13a so as to transmit an image signal containing each in-vivo image taken by the imaging unit 12a and an image signal containing the in-vivo image taken by the imaging unit 42a to the radio unit 13a successively and transmit the image signals at a predetermined transmission frame rate following an imaging order of the imaging units 12a, 42a. In this case, the control unit 45 transmits the in-vivo images of the subject 1 to the radio unit 13a successively at a transmission interval corresponding to the function unique to the capsule endoscope 2b. In the meantime, the control unit 45 may have a compression processing function for compressing the in-vivo images taken by the imaging units 12a, 42a and may transmit the image signals containing the compressed in-vivo image to the radio unit 13a successively by radio. Other function of the control unit 45 is the same as the control unit 15 of the capsule endoscope 2a of the first embodiment.

The power source circuit 14b and a magnetic switch 47 are installed to the control substrate 46 having the control unit 45, as well as the control unit 45. The control unit 46, the illumination substrates 11b, 41b, the imaging substrates 12b, 42b, the radio substrate 13c and the power source substrates 14c, 14d are connected electrically through a flexible circuit substrate.

Figure 15:
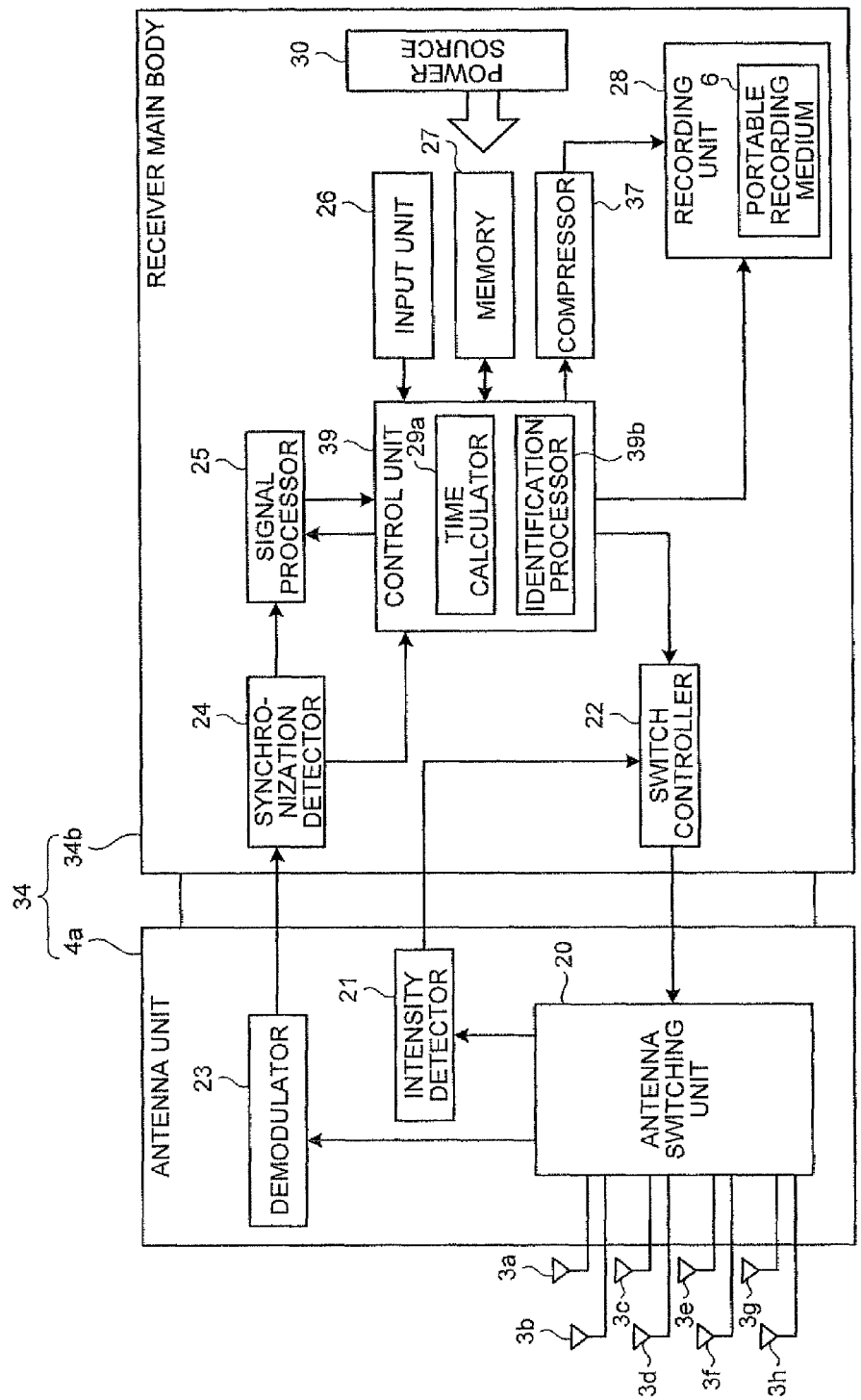
FIG. 15 is a block diagram showing schematically an example of the configuration of the receiving apparatus according to the second embodiment of the present invention.

Next, the configuration of the receiving apparatus 34 of the second embodiment of the present invention will be described. FIG. 15 is a block diagram showing schematically an example of the configuration of the receiving apparatus 34 of the second embodiment of the present invention. As shown in FIG. 15, the receiving apparatus 34 of the second embodiment includes a receiver main body 34b instead of the receiver main body 4b of the receiving apparatus 4 of the first embodiment. The receiver main body 34b includes a control unit 39 instead of the control unit 29 of the receiver main body 4b of the first embodiment and further includes a compressor 37 which compresses an in-vivo image. Other configuration is the same as the first embodiment and like reference numerals are attached to like components.

The compressor 37 compresses non-compressed image in the in-vivo images received from the capsule endoscopes 2a, 2b. More specifically, the compressor 37 compresses the in-vivo images in a non-compression state acquired from the control unit 39 under a control of the control unit 39 successively and transmits each compressed in-vivo image (compressed image) to the recording unit 28 successively. In this case, the in-vivo images compressed by the compressor 37 are recorded successively in the portable recording medium 6 in conditions in which they are identified depending on the function unique to the capsule endoscope 2a or the function unique to the capsule endoscope 2b.

The control unit 39 is achieved using a CPU for executing a processing program, a ROM in which the processing program is stored preliminarily and a RAM for storing therein arithmetic operation parameter and the like so as to control each component of the receiver 34. The control unit 39 has the time calculator 29a and an identification processor 39b for identifying the in-vivo image depending on the function unique to the capsule endoscope 2a and the function unique to the capsule endoscope 2b instead of the identification processor 29b for identifying the in-vivo image depending on the function unique to the monocular capsule endoscope 2a. The control unit 39 calculates a time interval (transmission interval of each in-vivo image) corresponding to the function of the capsule endoscope 2a or the function unique to the capsule endoscope 2b so as to identify the in-vivo images of the subject 1 depending on the functions unique to the capsule endoscopes 2a, 2b based on the acquired time interval. The control unit 39 controls the recording unit 28 so as to record the in-vivo images of the subject 1 in the portable recording medium 6 such that they are identified depending on the functions unique to the capsule endoscopes 2a, 2b. Other functions of the control unit 39 are the same as the control unit 29 of the receiving apparatus 4 of the first embodiment.

The identification processor 39b identifies the in-vivo image (in-vivo image of the subject 1) generated and output successively by the signal processor 25 depending on the functions unique to the capsule endoscopes 2a, 2b based on the time interval calculated by the time calculator 29a. If the in-vivo image of the subject 1 is an image taken by the capsule endoscope 2a, the identification processor 39b identifies the in-vivo image depending on the function unique to the capsule endoscope 2a in the same way as the identification processor 29b of the receiving apparatus 4 of the first embodiment. On the other hand, if the in-vivo image of the subject 1 is an image taken by the capsule endoscope 2b, the identification processor 39b identifies the in-vivo image depending on the function unique to the capsule endoscope 2b and further identifies the in-vivo images depending on the imaging units. The identification processor 39b determines by which the in-vivo image acquired from the signal processor 25 is taken by the capsule endoscope 2a or 2b based on a combination of the time intervals calculated successively by the time calculator 29a.

The time interval between the in-vivo images calculated by the time calculator 29a is a time interval between the in-vivo images by the monocular capsule endoscope 2a or the binocular capsule endoscope 2b, that is, a time interval corresponding to the functions unique to the capsule endoscopes 2a, 2b.

Figure 16:
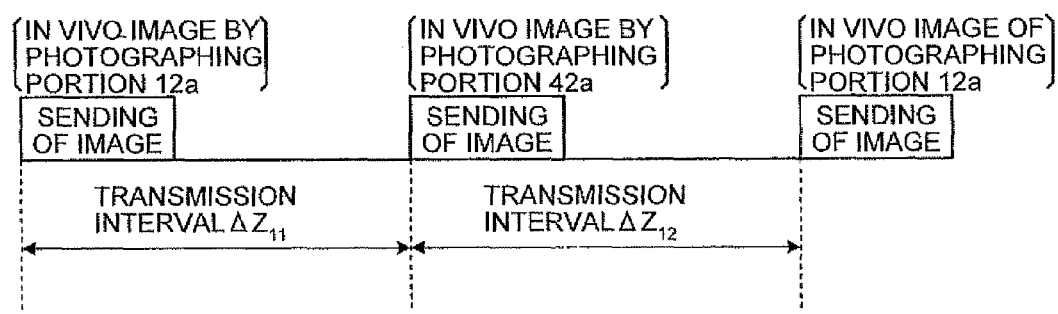
FIG. 16 is a schematic view exemplifying a transmission sequence of binocular capsule endoscope for transmitting each in-vivo image of a subject successively by radio.

Next, the operation of the binocular capsule endoscope 2b of the second embodiment will be described. FIG. 16 is a schematic view exemplifying a transmission sequence of the binocular capsule endoscope 2b which transmits the in-vivo images of the subject 1 successively by radio. As shown in FIG. 16, the binocular capsule endoscope 2b transmits the in-vivo images of the subject 1 taken successively by the imaging units 12a, 42a at transmission intervals $\Delta Z_{11}$, $\Delta Z_{12}$ corresponding to the function unique to the capsule endoscope 2b following an imaging order of the imaging units 12a, 42a.

More specifically, when the capsule endoscope 2b is introduced into the inside of the organ of the subject 1, the control unit 45 makes the imaging units 12a, 42a take the in-vivo images at the first frame to the n frame (n: positive integer) following a predetermined imaging order and make the radio unit 13a transmit the in-vivo images from the first frame to the n frame successively by radio following the imaging order of the imaging units 12a, 42a. Here, the control unit 45, when it makes the imaging units, 12a, 42a take the in-vivo images from the first frame to the n frame alternately, controls the radio unit 13a to transmit the in-vivo images taken by the imaging unit 12a and the in-vivo images taken by the imaging unit 42a successively by radio at the transmission intervals $\Delta Z_{11}$, $\Delta Z_{12}$ following the imaging order of the imaging units 12a, 42a.

As shown in FIG. 16, for example, the control unit 45 controls the radio unit 13a to transmit the in-vivo image taken by the imaging unit 12a and the in-vivo image taken by the imaging unit 42a just after following this imaging order successively by radio at the transmission interval $\Delta Z_{11}$ and then controls the radio unit 13a to transmit the in-vivo image taken by the imaging unit 42a and the in-vivo image taken by the imaging unit 12a just after following this imaging order successively by radio at the transmission interval $\Delta Z_{12}$. The control unit 45 makes the radio unit 13a transmit the in-vivo images from the first frame to the n frame successively by radio by switching the transmission intervals $\Delta Z_{11}$, $\Delta Z_{12}$ following the imaging order of the imaging units 12a, 42a like a case of the in-vivo images of three frames.

In the meantime the transmission intervals $\Delta Z_{11}$ may be a time interval from start of transmitting of the in-vivo image of the imaging unit 12a by radio up to start of transmitting of the in-vivo image of the imaging unit 42a just thereafter by radio as shown in FIG. 16 or may be a time interval from end of transmitting of the in-vivo image of the imaging unit 12a up to end of transmitting of the in-vivo image of the imaging unit 42a just thereafter by radio. Likewise, the transmission interval $\Delta_{12}$ may be a time interval from start of transmitting of the in-vivo image of the imaging unit 42a to start of transmitting of the in-vivo image of the imaging unit 12a just thereafter or may be a time interval from end of transmitting of the in-vivo image of the imaging unit 42a to the end of transmitting of the in-vivo image of the imaging unit 12a just thereafter.

A combination of the transmission intervals $\Delta Z_{11}$, $\Delta Z_{12}$ of the in-vivo images continuous in the frame number is a combination of the time intervals corresponding to the functions unique to the binocular capsule endoscope 2b which acquires these in-vivo images and is uniquely set to this capsule endoscope 2b. That is, such a combination of the transmission intervals $\Delta Z_{11}$, $\Delta Z_{12}$ is time information which can specify the functions unique to the capsule endoscope 2b. As described above, the control unit 45 switches the transmission intervals $\Delta Z_{11}$, $\Delta Z_{12}$ successively following the imaging order of the imaging units 12a, 42a and makes the radio unit 13a transmit the in-vivo images from the first frame to the n frame successively by radio. As a result, the capsule endoscope 2b can transmit the in-vivo images of the subject 1 taken by the imaging units 12a, 42a successively by radio to the receiving apparatus 34 and notify the receiving apparatus 34 of the functions unique to the capsule endoscope 2b depending on the combination of the transmission intervals $\Delta Z_{11}$, $\Delta Z_{12}$ of the respective in-vivo images.

In the meantime, the transmission frame rate of the radio unit 13a which transmits the in-vivo images of the subject 1 at the aforementioned transmission intervals $\Delta Z_{11}$, $\Delta Z_{12}$ successively by radio is 2 [frame/second] if the sum of the transmission intervals $\Delta Z_{11} \Delta Z_{12}$ continuous as shown in FIG. 16 is a unit time (=1 second). On the other hand, the imaging frame rate of the imaging units 12a, 42a for taking the in-vivo images of the subject 1 may be of the same value as this transmission frame rate or of a different value as long as it uniquely corresponds to the transmission frame rate of the radio unit 13a.

The operation of the receiving apparatus 34 of the second embodiment of the present invention will be described. The receiving apparatus 34 of this second embodiment receives the in-vivo images of the subject 1 transmitted by radio by the monocular capsule endoscope 2a or the binocular capsule endoscope 2b as described above. The control unit 39 of the receiving apparatus 34 performs the procedure of the step S101 to S108 to identify and records the in-vivo images of the subject 1 received from the monocular capsule endoscope 2a or the binocular capsule endoscope 2b successively in the portable recording medium 6 depending on the functions unique to the capsule endoscopes 2a, 2b. In this case, the identification processor 39b determines an object (that is, the in-vivo image acquiring apparatus which takes the in-vivo image, the capsule endoscope 2a or 2b) which has taken the in-vivo image of the subject 1 based on a combination of the time intervals calculated by the time calculator 29a and identifies the in-vivo images depending on the function unique to the capsule endoscopes 2a, 2b. When it is determined that the object which has taken the in-vivo image of the subject 1 is the binocular capsule endoscope 2b, the identification processor 39b identifies the in-vivo images which have been identified depending on the function unique to the capsule endoscope 2b, further depending on the imaging units 12a, 42a.

Figure 17:
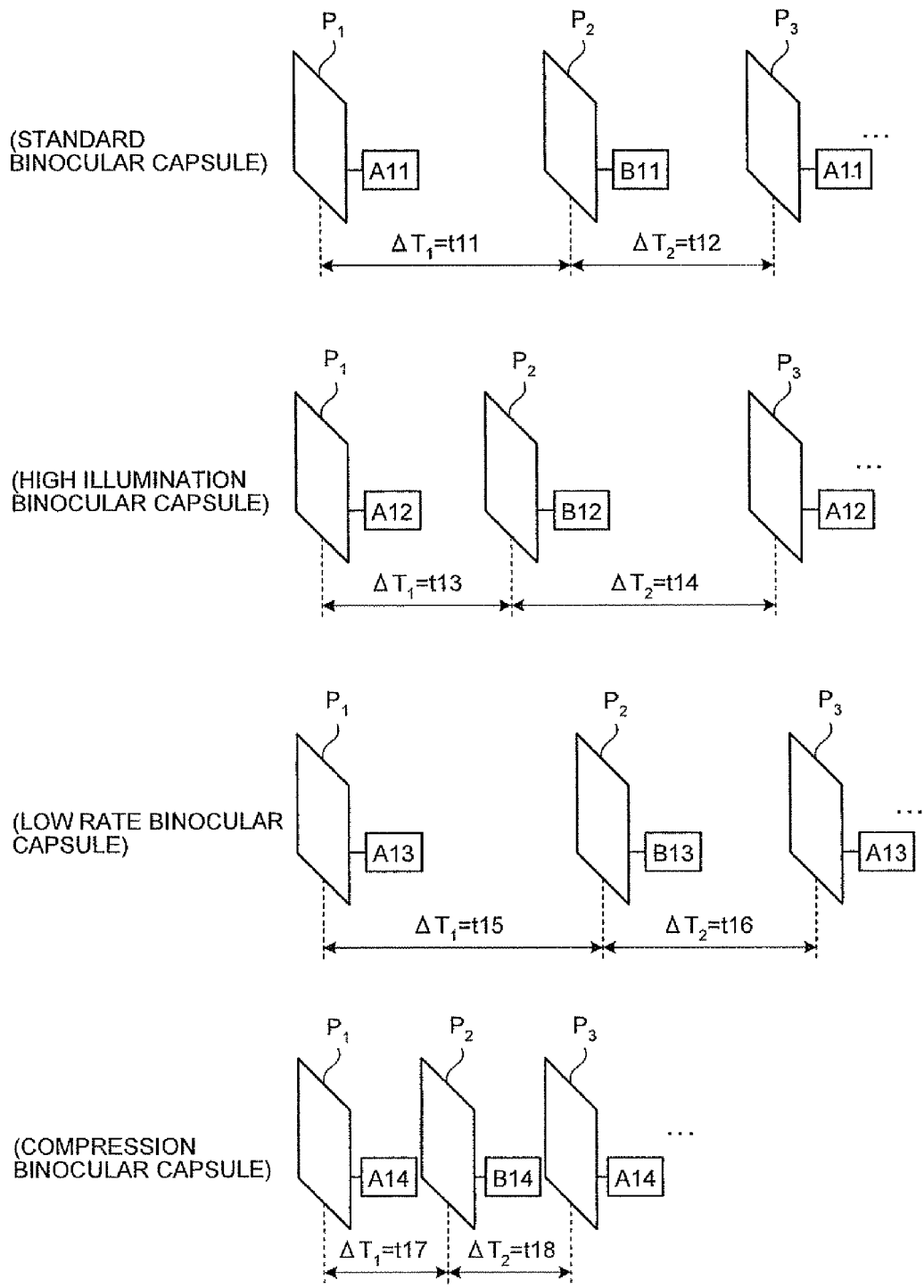
FIG. 17 is a schematic view for explaining an operation of the identification processor for identifying each in-vivo image depending on each function unique to the binocular capsule endoscope.

Hereinafter, the operation of the identification processor 39b which identifies the in-vivo image depending on the function unique to the capsule endoscope 2b will be described by exemplifying the function unique to the binocular capsule endoscope 2b. FIG. 17 is a schematic view for explaining an operation of the identification processor 39b for identifying each in-vivo image depending on each function unique to the binocular capsule endoscope 2b. If the object which has taken the in-vivo image of the subject 1 is a monocular capsule endoscope 2a, the identification processor 39b identifies the in-vivo image depending on the function unique to the capsule endoscope 2a like the identification processor 29b of the receiving apparatus 4 of the first embodiment.

When the capsule endoscope 2b inside the subject 1 transmits the in-vivo images from the first frame to the third frame successively at the transmission intervals $\Delta Z11$, $\Delta Z12$ (see FIG. 16) by radio as described above, the receiving apparatus 34 receives the in-vivo images from the first frame to the third frame successively. In this case, the time calculator 29a calculates a time interval $\Delta T1$ between time information T2 of in-vivo image P2 at the second frame and time information T1 of in-vivo image P1 at the first frame and then, calculates a time interval $\Delta T2$ between time information T3 of in-vivo image P3 at the third frame and time information T2 of in-vivo image P2 at the second frame. The identification processor 39b identifies the in-vivo images P1, P2, P3 of the subject 1 depending on the function unique to the capsule endoscope 2b based on a combination of the time intervals $\Delta T1$, $\Delta T2$ calculated by the time calculator 29a. The combination of the time intervals $\Delta T1$, $\Delta T2$ corresponds to a combination of transmission intervals $\Delta Z11$, $\Delta Z_{12}$ corresponding to the function unique to the capsule endoscope 2b.

As the types of the binocular capsule endoscope 2b depending on the functions, for example, standard binocular capsule, high illumination binocular capsule, low rate binocular capsule and compression binocular are exemplified. In the meantime, the standard binocular capsule is a capsule endoscope which has two imaging units (for example, imaging units 12a, 42a shown in FIG. 14) for taking the in-vivo images of the subject 1 and takes the in-vivo images of the subject 1 successively at a standard imaging frame rate (for example, 2 [frame/second]) by illuminating the inside of the organ of the subject 1 with standard illumination light intensity. The high illumination binocular capsule is a capsule endoscope which illuminates the inside of the organ of the subject 1 with higher illumination light intensity than the standard binocular capsule and has the same function as the standard binocular capsule as other function (number of possessed imaging units and imaging frame rate). Such a high illumination binocular capsule is suitable for the capsule endoscope which takes images inside the organ forming a large space like the stomach. In the meantime, the illumination mechanism of the high illumination binocular capsule is the same as the above-mentioned high illumination monocular capsule.

The low rate binocular capsule is a capsule endoscope which takes the in-vivo images of the subject 1 successively at a lower speed imaging frame rate than the standard binocular capsule and has the same function as the standard binocular capsule as other function (number of possessed imaging units and illumination light intensity). Such a low rate binocular capsule is suitable for a capsule endoscope which takes the images of the inside of the organ which takes a longer time to pass through such as the small intestine and the large intestine. The compression binocular capsule is a capsule endoscope which transmits the compressed images obtained by compressing the in-vivo images taken successively by two imaging units, so that the in-vivo images of the subject 1 are transmitted successively by radio at a higher speed transmission frame rate than the standard binocular capsule and has the same function as the standard binocular capsule as other function (number of possessed imaging units and illumination light intensity and the like). The compression binocular capsule is suitable for a capsule endoscope which transmits the in-vivo images in a large number of the inside of a desired organ in an area from the buccal cavity to the large intestine.

In case where the capsule endoscope 2b is a standard binocular capsule, the capsule endoscope 2b transmits the in-vivo images $P_1$, $P_2$ at, for example, a transmission interval $\Delta Z_{11}$=t11 [second] successively by radio and then, transmits the in-vivo images $P_2$, $P_3$ at a transmission interval $\Delta Z_{12}$=t12 [second] successively by radio. In this case, the time calculator 29a calculates the time interval $\Delta T_1$=t11 of the in-vivo images $P_1$, $P_2$ and the time interval $\Delta T_2$=t12 of the in-vivo images $P_2$, $P_3$ successively.

As shown in FIG. 17, the identification processor 39b determines that the object which has taken the in-vivo images $P_1$, $P_2$, $P_3$ is the binocular capsule endoscope 2b based on the combination (t11, t12) of the time intervals $\Delta T_1$, $\Delta T_2$ calculated by the time calculator 29a and then determines that the function unique to the capsule endoscope 2b is the function of the standard binocular capsule The identification processor 39b adds identification information A11, B11 indicating an in-vivo image corresponding to this determined function (standard binocular capsule) to the in-vivo images $P_1$, $P_2$, $P_3$. In this case, the identification processor 39b adds identification information A11 indicating the in-vivo image of the imaging unit 12a to the in-vivo image $P_1$ of the in-vivo images $P_1$, $P_2$, $P_3$, identification information B11 indicating the in-vivo image of the imaging unit 42a to the in-vivo image $P_2$ and identification information A11 indicating the in-vivo image of the imaging unit 12a to the in-vivo image $P_3$. In this way, the identification processor 39b identifies the in-vivo images $P_1$, $P_2$, $P_3$ of the subject 1 depending on the function unique to the standard binocular capsule and further identifies the in-vivo images $P_1$, $P_2$, $P_3$ depending on the imaging unit 12a, 42a.

On the other hand, if the capsule endoscope 2b is a high illumination binocular capsule, the capsule endoscope 2b transmits the in-vivo images $P_1$, $P_2$ at a transmission interval $\Delta Z_{11}$=t13 [second] for example, successively by radio and then transmits the in-vivo images 22, $P_3$ at a transmission interval $\Delta Z_{12}$=t14 [second] successively by radio. In this case, the time calculator 29a calculates the time interval $\Delta T_1$=t13 of the in-vivo images $P_1$, $P_2$ and the time interval $\Delta T_2$=t14 of the in-vivo images $P_2$, $P_3$ successively. In the meantime, if a sum (t11+t12) of the transmission intervals $\Delta Z_{11}$, $\Delta Z_{12}$ of the aforementioned standard binocular capsule is a unit time, a sum (t13+t14) of the transmission intervals $\Delta Z_{11}$, $\Delta Z_{12}$ of the high illumination binocular capsule is of substantially the same value as the sum (t11+t12) of the transmission intervals $\Delta Z_{11}$, $\Delta Z_{12}$ of the standard binocular capsule.

As shown in FIG. 17, the identification processor 39b determines that the source which takes the in-vivo images $P_1$, $P_2$, $P_3$ is the binocular capsule endoscope 2b based on the combination (t13, t14) of the time intervals $\Delta T1$, $\Delta T_2$ calculated by the time calculator 29a and then determines that the function unique to the capsule endoscope 2b is the function of the high illumination binocular capsule. The identification processor 39b adds identification information A12, B12 indicating an in-vivo image corresponding to this determined function (high illumination binocular capsule) to the in-vivo images $P_1$, $P_2$, $P_3$. In this case, the identification processor 39b adds identification information A12 indicating the in-vivo image of the imaging unit 12a to the in-vivo image $P_1$ of the in-vivo images $P_1$, $P_2$, $P_3$, identification information B12 indicating the in-vivo image of the imaging unit 42a to the in-vivo image $P_2$ and identification information A12 indicating the in-vivo image of the imaging unit 12a to the in-vivo image $P_3$. In this way, the identification processor 39b identifies the in-vivo images $P_1$, $P_2$, $P_3$ of the subject 1 depending on the function unique to the high illumination binocular capsule and further identifies the in-vivo images $P_1$, $P_2$, $P_3$ depending on the imaging unit 12a, 42a.

On the other hand, if the capsule endoscope 2b is a low rate binocular capsule, the capsule endoscope 2b transmits the in-vivo images $P_1$, $P_2$ at a transmission interval $\Delta Z_{11}$=t15 [second] for example, successively by radio and then transmits the in-vivo images $P_2$, $P_3$ at a transmission interval $\Delta Z_{12}$=t16 [second] successively by radio. In this case, the time calculator 29a calculates the time interval $\Delta T_1$=t15 of the in-vivo images $P_1$, $P_2$ and the time interval $\Delta T_2$=t16 of the in-vivo images $P_2$, $P_3$ successively. In the meantime, a sum (t15+t16) of the transmission intervals $\Delta Z_{11}$, $\Delta Z_{12}$ of the aforementioned low rate binocular capsule is larger than the sum (t11+t12) of the transmission intervals $\Delta Z_{11}$, $\Delta Z_{12}$ of the standard binocular capsule.

As shown in FIG. 17, the identification processor 39b determines that the source which has taken the in-vivo images $P_1$, $P_2$, $P_3$ is the binocular capsule endoscope 2b based on the combination (t15, t16) of the time intervals $\Delta T_1$, $\Delta T_2$ calculated by the time calculator 29a and then determines that the function unique to the capsule endoscope 2b is the function of the low rate binocular capsule. The identification processor 39b adds identification information A13, B13 indicating an in-vivo image corresponding to this determined function (low rate binocular capsule) to the in-vivo images $P_1$, $P_2$, $P_3$. In this case, the identification processor 39b adds identification information A13 indicating the in-vivo image of the imaging unit 12a to the in-vivo image $P_1$ of the in-vivo images $P_1$, $P_2$, $P_3$, identification information B13 indicating the in-vivo image of the imaging unit 42a to the in-vivo image $P_2$ and identification information A13 indicating the in-vivo image of the imaging unit 12a to the in-vivo image $P_3$. In this way, the identification processor 39b identifies the in-vivo images $P_1$, $P_2$, $P_3$ of the subject 1 depending on the function unique to the low rate binocular capsule and further identifies the in-vivo images $P_1$, $P_2$, $P_3$ depending on the imaging unit 12a, 42a.

On the other hand, if the capsule endoscope 2b is a compression binocular capsule, the capsule endoscope 2b transmits the in-vivo images $P_1$, $P_2$ at a transmission interval $\Delta Z_{11}$=t17 [second] for example, successively by radio and then transmits the in-vivo images $P_2$, $P_3$ at a transmission interval $\Delta Z_{12}$=t18 [second] successively by radio. In this case, the time calculator 29a calculates the time interval $\Delta T_1$=t17 of the in-vivo images $P_1$, $P_2$ and the time interval $\Delta T_2$=t18 of the in-vivo images $P_2$, $P_3$ successively. In the meantime, a sum (t17+t18) of the transmission intervals $\Delta Z_{11}$, $\Delta Z_{12}$ of the aforementioned compression binocular capsule is smaller than the sum (t11+t12) of the transmission intervals $\Delta Z_{11}$, $\Delta Z_{12}$ of the standard binocular capsule.

As shown in FIG. 17, the identification processor 39b determines that the object which has taken the in-vivo images $P_1$, $P_2$, $P_3$ is the binocular capsule endoscope based on the combination (t17, t18) of the time intervals $\Delta T_1$, $\Delta T_2$ calculated by the time calculator 29a and then determines that the function unique to the capsule endoscope 2b is the function of the compression binocular capsule. The identification processor 39b adds identification information A14, B14 indicating an in-vivo image corresponding to this determined function (compression binocular capsule) to the in-vivo images $P_1$, $P_2$, $P_3$. In this case, the identification processor 39b adds identification information A14 indicating the in-vivo image of the imaging unit 12a to the in-vivo image $P_1$ of the in-vivo images $P_1$, $P_2$, $P_3$, identification information B14 indicating the in-vivo image of the imaging unit 42a to the in-vivo image $P_2$ and identification information A14 indicating the in-vivo image of the imaging unit 12a to the in-vivo image $P_3$. In this way, the identification processor 39b identifies the in-vivo images $P_1$, $P_2$, $P_3$ of the subject 1 depending on the function unique to the compression binocular capsule and further identifies the in-vivo images $P_1$, $P_2$, $P_3$ depending on the imaging unit 12a, 42a.

In the meantime, the time calculator 29a calculates the time intervals $\Delta T_3, \ldots, \Delta T_{n-2}, \Delta T_{n-1}$ of the in-vivo images subsequent to the third frame like the above-described $\Delta T_1$, $\Delta T_2$ successively. The identification processor 39b identifies the in-vivo images $P_3$, $P_{n-1}$, $P_n$ subsequent to the third frame depending on the function unique to the capsule endoscope 2b based on the combination of the time intervals ($\Delta T_3$, $\Delta T_4$), ..., ($\Delta T_{n-2}$, $\Delta T_{n-1}$) calculated by the time calculator 29a successively like the in-vivo images $P_1$, $P_2$, $P_3$ from the first frame to the third frame.

The in-vivo image identified by the identification processor 39b is recorded successively in the portable recording medium 6 in the recording unit 28 as described above. In this case, if the identified in-vivo image is a compressed image, that is, an in-vivo image supplied with any one of the identification images A14, B14, the identification processor 39b records the compressed image (the in-vivo images compressed preliminarily by the capsule endoscope 2b) in the portable recording medium 6 without making the compressor 37 perform the compression processing. On the other hand, if the identified in-vivo image is a non-compressed image, that is, an in-vivo image supplied with neither the identification information A14 nor B14, the identification processor 39b makes the compressor 37 perform the compression processing and records the in-vivo image (compressed image) compressed by the compressor 37 in the portable recording medium 6.

Although according to the second embodiment of the present invention, the binocular capsule endoscope 2b is exemplified as an example of the compound eye in-vivo image acquiring apparatus, the present invention is not limited to this example, but the number of the imaging units possessed by the compound eye in-vivo image acquiring apparatus may be three or more. That is, the aforementioned capsule endoscope 2b is any compound eye in-vivo image acquiring apparatus having plural imaging units. In this case, the number of the transmission intervals corresponding to the function unique to the compound eye capsule endoscope 2b is increased depending on the number of the possessed imaging units. The compound eye capsule endoscope 2b transmits the in-vivo images successively by radio following an imaging order of the plural imaging units at a transmission interval contained in the combinations increased corresponding to the number of the possessed imaging units. On the other hand, the identification processor 39b of the receiving apparatus 34 acquires a combination of the time intervals of the in-vivo images corresponding to a combination of the transmission intervals increased corresponding to the number of the possessed imaging units and identifies the in-vivo images depending on the function unique to the compound eye capsule endoscope 2b and the imaging units based on the combination of the acquired time intervals.

According to the second embodiment of the present invention, as described above, when transmitting the in-vivo images of the subject taken by the plurality of the imaging units to outside successively by radio, the in-vivo images are transmitted successively by radio following an imaging order of the imaging unit at a time interval corresponding to the function unique to the device classified by the number of possessed imaging units, the frame rate, illumination light intensity, necessity of image compression processing and the like. Thus, the function unique to the device and the object (imaging unit) which has taken each in-vivo image can be notified to outside by a combination of the time intervals of the in-vivo images transmitted successively by radio even if no identification information corresponding to the function unique to the device is attached to each image signal. As a result, the same operating effect as the first embodiment can be enjoyed and the compound eye in-vivo image acquiring apparatus capable of identifying the in-vivo images depending on the function unique to the device and the imaging units can be achieved without increasing the amount of information when the in-vivo images taken by the plurality of the imaging units are transmitted by radio.

Further, the compound eye in-vivo image acquiring apparatus receives the in-vivo images of the subject successively, detects the time information for specifying the received in-vivo image successively, calculates the time intervals of the in-vivo images based on this detected time information so as to acquire a combination of the time intervals corresponding to the function unique to the in-vivo image acquiring apparatus and the imaging order and then, identifies the in-vivo images of the subject based on this acquired combination of the time intervals. Thus, the in-vivo image of the subject can be identified depending on the function unique to the in-vivo image acquiring apparatus and the imaging unit based on the combination of the time intervals of the in-vivo images received in succession, even if no identification information indicating the function unique to the device is received from the in-vivo image acquiring apparatus. Consequently, the same operating effect as the first embodiment can be enjoyed and the receiving apparatus capable of identifying the in-vivo images of the subject depending on the function unique to the compound eye in-vivo image acquiring apparatus and the imaging unit can be achieved without increasing the amount of information when the in-vivo images which the compound eye in-vivo image acquiring apparatus acquires with the plural imaging units are transmitted successively by radio.

Further, the same operating effect as the first embodiment can be enjoyed by providing the compound eye in-vivo image acquiring apparatus and the receiving apparatus and the in-vivo image acquiring system capable of acquiring the in-vivo images which can be identified depending on the function unique to the in-vivo image acquiring apparatus and the imaging unit can be achieved without increasing the amount of information when the in-vivo images of the subject taken with the plural imaging units are transmitted by radio.

According to the in-vivo image acquiring apparatus, the receiving apparatus and the in-vivo image acquiring system of the present invention, the amount of information when the in-vivo image of the subject taken by the plural imaging units is transmitted by radio can be reduced as much as possible and consequently, consumption power when transmitting the in-vivo images of the subject by radio can be suppressed to a possible extent and the saving of power in the compound eye in-vivo image acquiring apparatus can be accelerated. Further, the in-vivo images of the subject can be accumulated successively in conditions in which they are identified depending on the function unique to the compound eye in-vivo image acquiring apparatus and the imaging unit. Further, the in-vivo images can be displayed on the image display unit such that they are classified depending on the function unique to the in-vivo image acquiring apparatus and the imaging unit by taking in the accumulated in-vivo images into the image display unit. As a result, the in-vivo images of the subject taken by the plural imaging units each having a different image pickup field can be observed easily and effectively.

Next, a third embodiment of the present invention will be described. Although in the second embodiment, the in-vivo images are identified based on a combination of the time intervals of the in-vivo images calculated by the time calculator $29a$, the third embodiment is provided with a data table indicating a correspondence relationship between the combination of the time intervals of the in-vivo image and the function unique to the in-vivo image acquiring apparatus and determines the function of the in-vivo image acquiring apparatus corresponding to a combination of the time intervals by referring to this data table, so as to identify the in-vivo images depending on this determined function.

Figure 18:
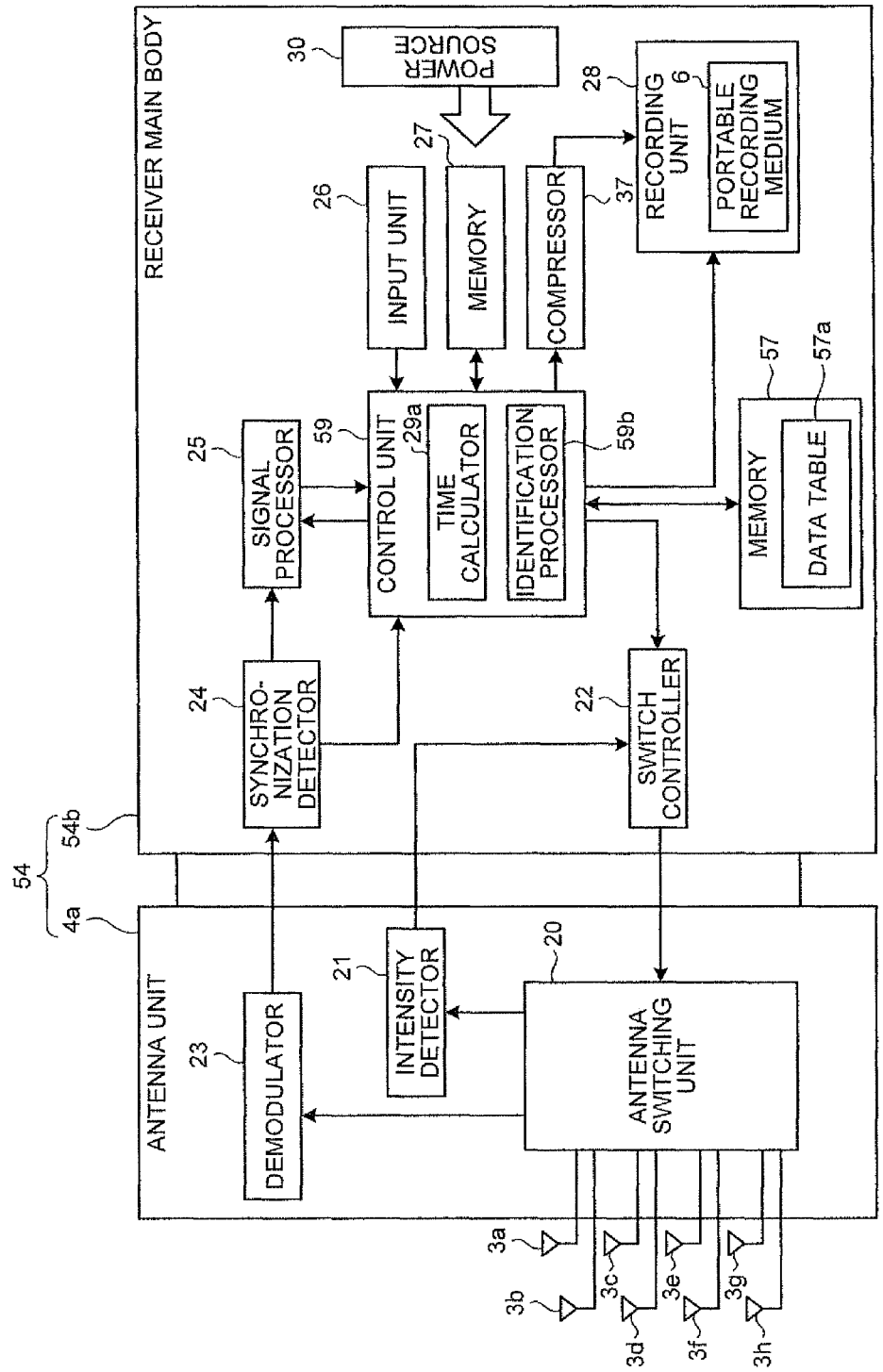
FIG. 18 is a block diagram showing an example of the configuration of the receiving apparatus according to a third embodiment of the present invention.

FIG. 18 is a block diagram showing an example of the configuration of a receiving apparatus of the third embodiment of the present invention. As shown in FIG. 18, the receiving apparatus 54 of the third embodiment includes a receiver main body $54b$ instead of the receiver main body $34b$ of the receiving apparatus 34 of the second embodiment. This receiver main body $54b$ includes a control unit 59 instead of the control unit 39 of the receiver main body $34b$ of the second embodiment and a memory 57 which stores a data table $57a$ indicating the correspondence relationship between the combination of the time intervals of the in-vivo images and the function unique to the capsule endoscope $2a$. Other configuration is the same as the second embodiment and like reference numerals are attached to like components. The in-vivo image acquiring system of the third embodiment of the present invention includes the receiving apparatus 54 instead of the in-vivo image acquiring system (see FIG. 13) of the second embodiment.

The memory 57 stores the data table $57a$ in which the correspondence relationship between the combination of the time intervals of the in-vivo image and the function unique to the capsule endoscope $2a$, $2b$ and transmits the data table $57a$ to the control unit 59 under a control of the control unit 59. The data table $57a$ shows the correspondence relationship between the combination of the time intervals of the continuous in-vivo images and the function unique to the capsule endoscope $2a$, $2b$ as shown in FIG. 19. The combination of the time intervals shown in the data table $57a$ is a combination ($\Delta T_{n-2}$, $\Delta T_{n-1}$) of the time interval between the continuous in-vivo images $P_{n-2}$, $P_{n-1}$ and $P_n$ calculated by the time calculator $29a$ and corresponds to any one of the combination of the transmission intervals $\Delta Z_1$, $\Delta Z_2$ corresponding to the function unique to the capsule endoscope $2a$ or the combination of the transmission intervals $\Delta Z_{11}$, $\Delta Z_{12}$ corresponding to the function unique to the capsule endoscope $2b$.

The control unit 59 is constituted of a CPU for executing processing program, a ROM which stores therein the processing program preliminarily and a RAM which stores therein arithmetic operation parameter and the like so as to control respective components of the receiving apparatus 54. The control unit 59 includes the time calculator $29a$ and instead of the identification processor $39b$ of the receiving apparatus 34 of the second embodiment, contains a identification processor $59b$ for identifying the in-vivo image depending on the function unique to the capsule endoscope $2a$, $2b$ by referring to the data table $57a$. More specifically, the control unit 59 calculates a time interval (transmission interval of the in-vivo image) corresponding to the function unique to the capsule endoscope $2a$, $2b$ based on the time information of the in-vivo images acquired successively from the synchronization detector 24 and identifies the in-vivo images of the subject 1 depending on the function unique to the capsule endoscope $2a$, $2b$ based on the acquired time interval and data table $57a$. Other function of the control unit 59 is the same as the control unit 39 of the receiving apparatus 34 of the second embodiment.

The identification processor $59b$ identifies the in-vivo images (in-vivo image of the subject 1) generated and output successively by the signal processor 25 depending on the function unique to the capsule endoscope $2a$, $2b$ based on the time intervals calculated by the time calculator $29a$ and the data table $57a$. More specifically, the identification processor $59b$ acquires a combination ($\Delta T_{n-2}$, $\Delta T_{n-1}$) of the time intervals between the continuous in-vivo images $P_{n-2}$, $P_{-1}$ and $P_n$ calculated by the time calculator $29a$. The identification processor $59b$ reads out the data table $57a$ from the memory 57 as required and determines the function unique to the capsule endoscope $2a$, $2b$ corresponding to the combination ($\Delta T_{n-2}$, $\Delta T_{n-1}$) of the time intervals by referring to the read data table $57a$. The identification processor $59b$ identifies the in-vivo images depending on the function unique to the determined capsule endoscope (function unique to any of the capsule endoscopes $2a$, $2b$). Other function of the identification processor $59b$ is the same as the identification processor $39b$ of the receiving apparatus 34 of the second embodiment.

Next, the operation of the receiving apparatus 54 of the third embodiment will be described. The receiving apparatus 54 of the third embodiment receives the in-vivo images of the subject 1 transmitted by radio by the monocular capsule endoscope $2a$ or the binocular capsule endoscope $2b$. The control unit 59 of the receiving apparatus 54 repeats the procedure of the step S101 to S108 so as to identify the in-vivo images of the subject 1 received from the monocular capsule endoscope $2a$ or the binocular capsule endoscope $2b$ depending on the function unique to the capsule endoscope $2a$, $2b$ and records successively in the portable recording medium 6. In this case, the identification processor $59b$ determines the function unique to the capsule endoscope $2a$, $2b$ corresponding to the combination of the time interval calculated by the time calculator $29a$ by referring to the data table $57a$ in the step S106 and identifies the in-vivo images depending on this determined functions. If the object which has taken the in-vivo image of the subject 1 is a binocular capsule endoscope $2b$, the identification processor $59b$ further identifies the in-vivo image identified depending on the function unique to the capsule endoscope $2b$, depending on the imaging units $12a$, $42a$.

Here, the operation of the identification processor $59b$ which identifies the in-vivo images of the subject 1 depending on the function unique to the capsule endoscope $2a$, $2b$ will be described specifically by referring to an example of the data table $57a$ shown in FIG. 19. If the time calculator $29a$ calculates the time intervals $\Delta T_{n-2}$, $\Delta T_{n-1}$ of the continuous in-vivo images $P_{n-2}$, $P_{n-1}$, $P_n$, the identification processor $59b$ determines the function unique to the capsule endoscope $2a$, $2b$ corresponding to the combination of the time intervals $\Delta T_{n-2}$, $\Delta T_{n-1}$ by referring to the data table $57a$.

More specifically, if the combination of the time interval $\Delta T_{n-2}$, $\Delta T_{n-1}$ is, for example, (t1+t1), the identification processor 59b determines that the object which has taken the in-vivo images $P_{n-2}, P_{n-1}, P_n$ is a capsule endoscope 2a which is a standard monocular capsule. In this case, the identification processor 59b adds identification information A1 indicating the in-vivo image corresponding to this determined function (standard monocular capsule) to the in-vivo images $P_{n-2}, P_{n-1}$ and $P_n$ so as to identify the in-vivo images $P_{n-2}, P_{n-1}$ and $P_n$ depending on the functions unique to the standard monocular capsule.

If the combination of the time intervals $\Delta T_{n-2}$, $\Delta T_{n-1}$ of the in-vivo images is other than (t1, t1), the identification processor 59b determines the function unique to the capsule endoscope corresponding to the combination of the time intervals of the in-vivo images shown in FIG. 19. It is determined that the function unique to the capsule endoscope corresponding to the combination of the time intervals of the in-vivo images is any one of the standard monocular capsule, high illumination monocular capsule, high rate monocular capsule, low rate monocular capsule, standard binocular capsule, high illumination binocular capsule, low rate binocular capsule and compression binocular capsule by the identification processing of the identification processor 59b. The identification processor 59b adds identification information (the aforementioned identification information A2, A3, A4, A11, A12, A13, A14, B11, B12, B13, B14) corresponding to this determined function like the cases of the first and second embodiments. Consequently, the identification processor 59b identifies the in-vivo images of the subject 1 depending on the functions unique to the capsule endoscope 2a, 2b and the imaging units.

The in-vivo images identified by the identification processor 59b are recorded successively into the portable recording medium 6 in the recording unit 28 like the first and second embodiments. If the identified in-vivo image is a compressed image, that is, the function unique to the capsule endoscope corresponding to the combination of the time intervals of the in-vivo images is a compression binocular capsule, the identification processor 59b records the compressed image in the portable recording medium 6 without making the compressor 37 compress such a compressed image. On the other hand, if the identified in-vivo image is a non-compressed image, that is, the function unique to the capsule endoscope corresponding to the combination of the time intervals of the in-vivo images is other than the compression binocular capsule, the identification processor 59b makes the compressor 37 compress such a non-compressed image and record that compressed in-vivo image (compressed image) in the portable recording medium 6.

Although according to the third embodiment, the in-vivo images are identified by referring to the data table 57a indicating the correspondence relationship between eight combinations of the time intervals and the functions unique to the capsule endoscope as shown in FIG. 19, the present invention is not limited to this example but the correspondence relationship between nine or more combinations of the time intervals and the functions unique to the capsule endoscope can be indicated by the data table 57a by complicating or classifying more in detail the correspondence relationship between the combinations of the time intervals of the in-vivo images indicated on the data table 57a and the function unique to the capsule endoscope. The identification processor 59b can identify the in-vivo images depending on the multiple functions unique to the capsule endoscope by referring to the data table 57a.

According to the third embodiment, as described above, when transmitting the in-vivo images taken with one or more imaging units successively by radio to outside, the in-vivo images are transmitted successively by radio following an imaging order of the imaging units at a time interval corresponding to the function of the device classified depending on the number of possessed imaging units, frame rate, illumination light intensity and whether or not the image compression processing is to be executed and the like. And the correspondence relationship between the combination of the time intervals of the in-vivo images and the function unique to the device is registered preliminarily in a data table which the receiving apparatus for receiving the in-vivo images holds and manages. Thus, the function unique to the device and the imaging unit for each in-vivo image can be notified to outside by a combination of the time intervals of the in-vivo images transmitted successively by radio even if no identification information corresponding to the function unique to the device is attached to each image signal. As a result, the same operating effect as the first and second embodiments can be enjoyed and the in-vivo image acquiring apparatus capable of easily identifying the in-vivo images depending on the function unique to the device can be achieved without increasing the amount of information when the in-vivo images taken by one or more imaging units are transmitted by radio.

Further, the data table in which the correspondence relationship between the combination of the time intervals of the in-vivo images and the function unique to the in-vivo image acquiring apparatus is possessed preliminarily and the function of the in-vivo image acquiring apparatus corresponding to the combination of the time intervals of the in-vivo images transmitted successively by radio by the in-vivo image acquiring apparatus is determined by referring to the data table while other configuration is constructed in the same way as the second embodiment. Consequently, the function of the in-vivo image acquiring apparatus corresponding to the combination of the time intervals of the in-vivo images received successively can be determined even if no identification information indicating the function of the device is received from the in-vivo image acquiring apparatus and the in-vivo image of the subject can be identified depending on this determined function and each imaging unit. As a result, the same operating effect as the first and second embodiments can be enjoyed and the receiving apparatus capable of identifying the in-vivo images of the subject easily depending on the function unique to the in-vivo image acquiring apparatus and the imaging unit can be achieved without increasing the amount of information when the in-vivo images which the in-vivo image acquiring apparatus acquires through the imaging units are transmitted successively by radio.

Further, the same operating effect as the first and second embodiments can be enjoyed by providing the in-vivo image acquiring apparatus and the receiving apparatus and the in-vivo image acquiring system capable of acquiring the in-vivo images which can be identified easily depending on the function unique to the in-vivo image acquiring apparatus and the imaging unit can be achieved without increasing the amount of information when the in-vivo images of the subject taken by one or more imaging units are transmitted by radio.

Next, a fourth embodiment of the present invention will be described. Although according to the second embodiment, the in-vivo images are identified based on a combination of the time intervals of the in-vivo images calculated by the time calculator 29a, according to the fourth embodiment, the function unique to the in-vivo image acquiring apparatus or the imaging unit related to each image are determined based on the time interval of the in-vivo image calculated by the time calculator 29a, and the in-vivo images are identified depending on the determined function and imaging unit.

Figure 20:
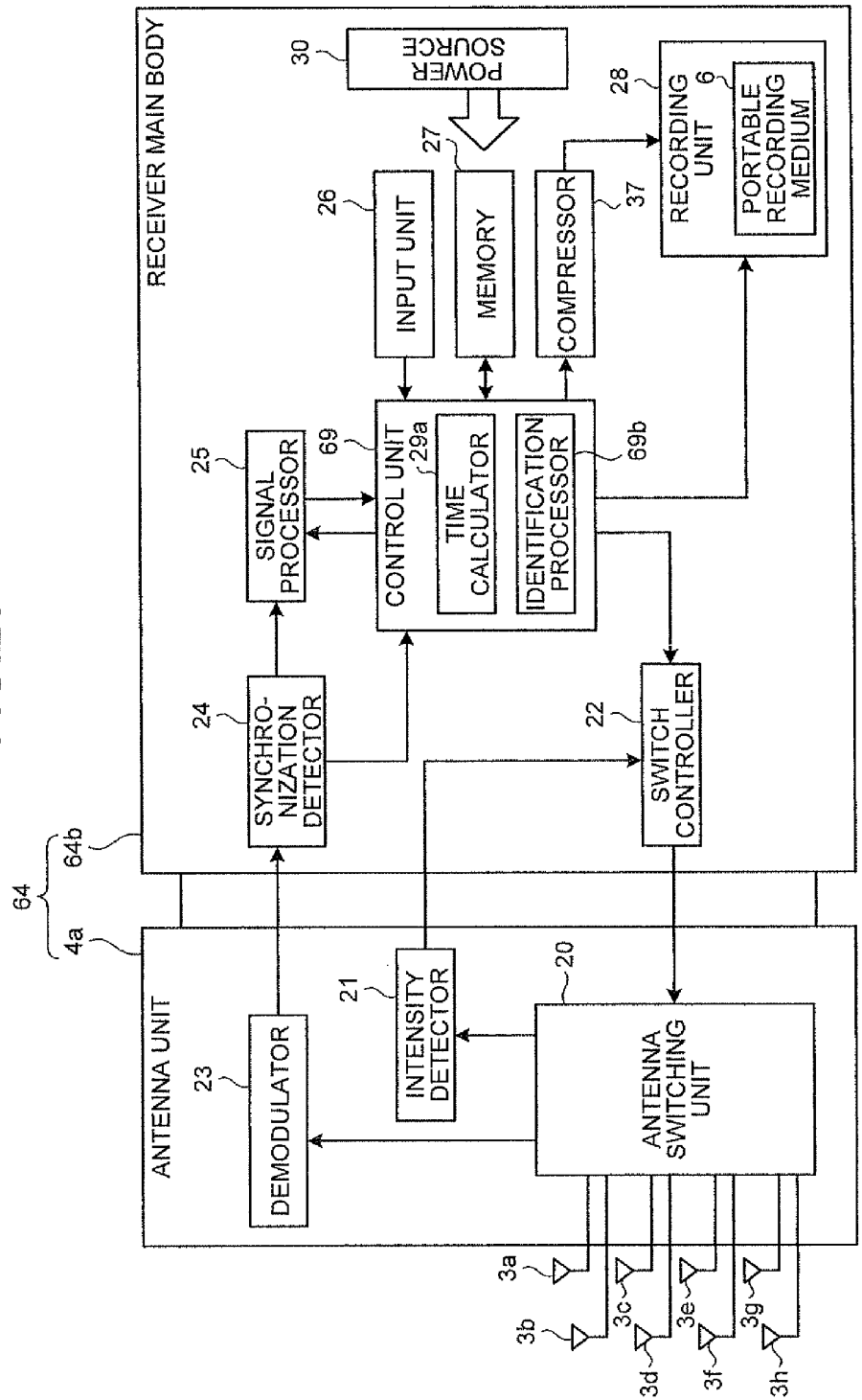
FIG. 20 is a block diagram showing an example of the configuration of the receiving apparatus according to a fourth embodiment of the present invention.

FIG. 20 is a block diagram showing an example of the configuration of the receiving apparatus according to the fourth embodiment of the present invention. As shown in FIG. 20, the receiving apparatus 64 of the fourth embodiment includes a receiver main body 64b instead of the receiver main body 34b of the receiving apparatus 34 of the second embodiment. This receiver main body 64b includes a control unit 69 instead of the control unit 39 of the receiver main body 34b of the second embodiment. Other configuration is the same as the second embodiment and like reference numerals are attached to like components. In the meantime, the in-vivo image acquiring system of the fourth embodiment of the present invention includes a receiving apparatus 64 instead of the receiving apparatus 34 of the in-vivo image acquiring system (see FIG. 13) of the second embodiment.

The control unit 69 is constituted of a CPU for executing processing program, a RON which stores therein the processing program preliminarily and a RAM which stores therein arithmetic operation parameter and the like so as to control respective components of the receiving apparatus 64. The control unit 69 includes the time calculator 29a and instead of the identification processor 39b of the receiving apparatus 34 of the second embodiment, contains an identification processor 69b. More specifically, the control unit 69 calculates a time interval (transmission interval of the in-vivo image) corresponding to the function unique to the capsule endoscope 2a, 2b based on the time information of the in-vivo images acquired successively from the synchronization detector 24 and identifies the in-vivo images of the subject 1 depending on the function unique to the capsule endoscope 2a, 2b based on the acquired time interval. Other function of the control unit 69 is the same as the control unit 39 of the receiving apparatus 34 of the second embodiment.

The identification processor 69b identifies the in-vivo images (in-vivo image of the subject 1) generated and output successively by the signal processor 25 depending on the function unique to the capsule endoscope 2a, 2b based on the time intervals calculated by the time calculator 29a. More specifically, the identification processor 69b acquires a time interval $\Delta T_{n-1}$ between the in-vivo images $P_{n-1}$ and $P_n$ calculated by the time calculator 29a. The identification processor 69b determines the function unique to the capsule endoscope 2a, 2b which is an imaging unit related to the in-vivo images $P_{n-1}$, $P_n$ based on the acquired time interval $\Delta T_{n-1}$. The identification processor 69b identifies the in-vivo images depending on the function unique to the determined capsule endoscope (function unique to any of the capsule endoscopes 2a, 2b). Other function of the identification processor 69b is the same as the identification processor 39b of the receiving apparatus 34 of the second embodiment.

Next, the operation of the receiving apparatus 64 of the fourth embodiment of the present invention will be described. FIG. 21 is a flow chart exemplifying the procedure which the control unit 69 of the receiving apparatus 64 of the fourth embodiment carries out. The receiving apparatus 64 receives the in-vivo images of the subject 1 transmitted by radio by the monocular capsule endoscope 2a or the binocular capsule endoscope 2b. The control unit 69 identifies the in-vivo images depending on the function unique to the capsule endoscope 2a, 2b based on the time interval of the in-vivo image of the subject 1 and records the identified in-vivo images into the portable recording medium 6.

As shown in FIG. 21, the control unit 69 acquires the in-vivo image of the subject 1 and the time information which specifies this in-vivo image (step S201) like the step S101, S102 and associates this acquired in-vivo image with the time information (step S202). In this case, the control unit 69 knows the correspondence relationship between the in-vivo image and the time information. The control unit 69 stores therein the associated in-vivo image and time information temporarily in the memory 27 and holds and manages the in-vivo images and time information such that they can be read out as required.

Next, the control unit 69 determines whether or not the in-vivo image associated with the time information in this step S202 is an in-vivo image at the first frame (step S203) like the above described step S103 and if it is the in-vivo image at the first frame (step S203: YES), the procedure returns to step S201, in which the procedure subsequent to this step S201 is repeated. On the other hand, unless the in-vivo image associated with the time information in the step S202 is any in-vivo image at the first frame (step S203: NO), the control unit 69 calculates a time interval between continuous two in-vivo images like the above-described step S104 (step S204). In this case, the time calculator 29a calculates a time interval $\Delta T_{n-1}$ between time information $T_n$ of the in-vivo image $P_n$ currently having a largest frame number and time information $T_{n-1}$ of the in-vivo image $P_{n-1}$ continuous with the in-vivo image $P_n$ and just before as described above. The control unit 69 stores therein the time interval $\Delta T_{n-1}$ calculated by the time calculator 29a temporarily in the memory 27.

After that, the control unit 69 identifies the in-vivo image based on the time interval calculated in step S204 (step S205). In this case, the identification processor 69b acquires the time interval $\Delta_{n-1}$ calculated by the time calculator 29a (read out from the memory 27). Here, the time interval $\Delta_{n-1}$ corresponds to transmission interval $\Delta Z_1$, $\Delta Z_2$ corresponding to the function unique to the capsule endoscope 2a or transmission interval $\Delta Z_{11}$, $\Delta Z_{12}$ corresponding to the function unique to the capsule endoscope 2b. Thus, the identification processor 69b can determine the function unique to the capsule endoscope 2a, 2b based on the acquired time interval $\Delta_{n-1}$ and identify the in-vivo images $P_{n-1}$, $P_n$ depending on this determined function. The identification processor 69b adds the identification information corresponding to the function (function unique to any one of the capsule endoscopes 2a and 2b) of the determined capsule endoscope to the in-vivo images $P_{n-1}$, $P_n$, so that the in-vivo images $P_{n-1}$, $P_n$ are identified depending on the function unique to the capsule endoscope.

Next, the control unit 69 controls the recording unit 28 to record the in-vivo image identified depending on the function unique to the capsule endoscope into the portable recording medium 6 (step S206) like the above-described step S107. In this case, the identification processor 69b records the in-vivo images $P_{n-1}$, $P_n$ in conditions in which they are supplied with identification information corresponding to the function unique to the capsule endoscope 2a, 2b into the portable recording medium 6 successively.

After that, the control unit 69 determines whether or not processing of all in-vivo images of the subject 1 is completed (step S207) like the above-described step S108 and if not (step S207: NO), the procedure returns to the step S201, in which the procedure subsequent to this step S201 is repeated. On the other hand, if it is determined that the processing is completed (step S207: YES), the control unit 69 terminates the processing.

Next, the operation of the identification processor 69b for identifying the in-vivo image depending on the function unique to the capsule endoscope 2a, 2b will be described in detail by exemplifying the standard monocular capsule and the standard binocular capsule as the aforementioned capsule endoscope 2a, 2b. FIG. 22 is a schematic view for explaining the operation of the identification processor 69b for identifying the in-vivo image depending on the function of the capsule endoscope 2a, 2b based on the time interval of each in-vivo image. If the time calculator 29a calculates the time interval $\Delta T_{n-1}$ of the continuous in-vivo images $P_{n-1}$, $P_n$, the identification processor 69b determines the function unique to the capsule endoscope 2a, 2b which is an object which has taken the in-vivo images $P_{n-1}$, $P_n$ and identifies the in-vivo images $P_{n-1}$, $P_n$ depending on the determined function.

More specifically, if the time interval $\Delta T_1$ between the in-vivo image $P_1$ at the first frame and the in-vivo image $P_2$ at the second frame is t1 substantially equal to the transmission interval $\Delta Z_1$, $\Delta Z_2$ corresponding to the function unique to the standard monocular capsule, the identification processor 69b determines that the object which has taken the in-vivo images $P_{n-1}$, $P_n$ is the capsule endoscope 2a as the standard monocular capsule and identifies the in-vivo images $P_1$, $P_2$ depending on the function unique to this determined standard monocular capsule. In this case, the identification processor 69b attaches identification information A1 to the in-vivo images $P_1$, $P_2$ like the first and second embodiments. After that, if the time interval $\Delta T_{n-1}$ of the in-vivo image is of substantially the same value as t1, the identification processor 69b adds the identification information A1 to the in-vivo images $P_3, \ldots, P_n$ subsequent to the third frame and identifies the in-vivo images depending on the function of the standard monocular capsule.

On the other hand, if the time interval $\Delta T_1$ between the in-vivo image $P_1$ at the first frame and the in-vivo image $P_2$ at the second frame is t11 substantially equal to the transmission interval $\Delta Z_{11}$ corresponding to the function unique to the standard binocular capsule, the identification processor 69b determines that the object which has taken the in-vivo images $P_1$, $P_2$ is the capsule endoscope 2a as the standard binocular capsule and identifies the in-vivo images $P_1$, $P_2$ depending on the function unique to this determined standard binocular capsule and the imaging unit. In this case, the identification processor 69b attaches identification information A11 to the in-vivo images $P_1$ on the head side of the in-vivo images $P_1$, $P_2$ and attaches the identification information B11 to the in-vivo images $P_2$ on the end side.

Subsequently, if the time interval $\Delta T_2$ between the in-vivo image $P_2$ at the second frame and the in-vivo image $P_3$ at the third frame is t12 substantially equal to the transmission interval $\Delta Z_{12}$ corresponding to the function unique to the standard binocular capsule, the identification processor 69b determines that the object which has taken the in-vivo images $P_2$, $P_3$ is the capsule endoscope 2b as the standard binocular capsule and identifies the in-vivo images $P_2$, $P_3$ depending on the function unique to this determined standard binocular capsule and the imaging unit. In this case, the identification processor 69b attaches identification information B11 to the in-vivo images $P_2$ on the head side of the in-vivo images $P_1$, $P_2$ and attaches the identification information A11 to the in-vivo images $P_3$ on the end side. After that, the identification processor 69b attaches the identification information A11, B11 to the in-vivo images $P_3, \ldots, P_n$ subsequent to the third frame if the time interval $\Delta T_{n-1}$ of the in-vivo image is substantially equal to t11 or t12 successively and identifies the in-vivo images depending on the function unique to the standard binocular capsule and the imaging unit.

In the meantime, the identification information A11 is identification information indicating an in-vivo image taken by the imaging unit 12a of the capsule endoscope 2a as the standard binocular capsule as described above. The identification information B11 is identification information indicating an in-vivo image taken by the imaging unit 42a of the capsule endoscope 2b as the standard binocular capsule as described above.

Here, as a type of the capsule endoscope 2b different in function, the high rate binocular capsule having the same function as the standard binocular capsule as other function (number of possessed imaging units, illumination light intensity, whether or not image compression processing is executed and the like), which takes the in-vivo images of the subject 1 successively at a higher speed frame rate than the standard binocular capsule will be exemplified. The capsule endoscope 2b as the high rate binocular capsule transmits the in-vivo images taken successively by the imaging units 12a, 42a successively by radio at transmission intervals $\Delta Z_{11}$, $\Delta Z_{12}$ (=t1/2) following an imaging order. In the meantime, the value t1/2 of the transmission intervals $\Delta Z_{11}$, $\Delta Z_{12}$ is a value half the value t1 of the transmission intervals $\Delta Z_1$, $\Delta Z_2$ corresponding to the standard monocular capsule.

When the receiving apparatus 64 receives the in-vivo images of the subject 1 successively from the capsule endoscope 2b as the high rate binocular capsule, the time calculator 29a calculates the time interval $\Delta T_{n-1}$ (=t1/2) of the in-vivo image. The time calculator 29a calculates an accumulated total of the time intervals $\Delta T_{n-1}$ calculated successively.

If the time interval $\Delta T_1$ between the in-vivo image $P_1$ at the first frame and the in-vivo image $P_2$ at the second frame is t1/2 substantially equal to the transmission intervals $\Delta Z_{11}$, $\Delta Z_{12}$ corresponding to the function unique to the high rate binocular capsule and the accumulated total of the time intervals is odd number times t1/2, the identification processor 69b determines that the object which has taken the in-vivo images $P_1$, $P_2$ is a capsule endoscope 2b as a high rate binocular capsule and identifies the in-vivo images $P_1$, $P_2$ depending on the function unique to the high rate binocular capsule and the imaging unit. In this case, the identification processor 69b attaches identification information A15 to the in-vivo image $P_1$ on the head side of the in-vivo images $P_1$, $P_2$ and attaches identification information B15 to the in-vivo image $P_2$ on the end side.

Next, If the time interval $\Delta T_2$ between the in-vivo image $P_2$ at the second frame and the in-vivo image $P_3$ at the third frame is t1/2 substantially equal to the transmission intervals $\Delta Z_{11}$, $\Delta Z_{12}$ corresponding to the function unique to the high rate binocular capsule and the accumulated total of the time intervals is even number times t1/2, the identification processor 69b determines that the object which has taken the in-vivo images $P_2$, $P_3$ is a capsule endoscope 2b as a high rate binocular capsule and identifies the in-vivo images $P_2$, $P_3$ depending on the function unique to the high rate binocular capsule and the imaging unit. In this case, the identification processor 69b attaches identification information B15 to the in-vivo image 22 on the head side of the in-vivo images $P_2$, $P_3$ and attaches identification information A15 to the in-vivo image $P_3$ on the end side.

In case of the in-vivo images $P_3, \ldots, P_n$ subsequent to the third frame, if the time interval $\Delta T_{n-1}$ between the in-vivo image $P_{n-1}$ and the in-vivo image $P_n$ just after is t1/2 substantially equal to the transmission intervals $\Delta Z_{11}$, $\Delta Z_{12}$ corresponding to the function unique to the high rate binocular capsule and the accumulated total is odd number times t1/2, the identification processor 69b attaches identification information A15 to the in-vivo image $P_{n-1}$ on the head side of the in-vivo images $P_{n-1}$, $P_n$ and attaches identification information B15 to the in-vivo image $P_n$ on the end side. On the other hand, if the time interval $\Delta T_{n-1}$ between the in-vivo image $P_{n-1}$ and the in-vivo image $P_n$ just after is t1/2 substantially equal to the transmission intervals $\Delta Z_{11}$, $\Delta Z_{12}$ corresponding to the function unique to the high rate binocular capsule and the accumulated total of the time intervals is even number times t1/2, the identification processor 69b attaches identification information B15 to the in-vivo image $P_{n-1}$ on the head side of the in-vivo images $P_{n-1}$, $P_n$ and attaches identification information A15 to the in-vivo image $P_n$ on the end side.

In the meantime, the identification information A15 is identification information indicating an in-vivo image taken by the imaging unit 12a of the capsule endoscope 2b which is a high rate binocular capsule. The identification information B15 is identification information indicating an in-vivo image taken by the imaging unit 42a of the capsule endoscope 2b which is a high rate binocular capsule.

The identification processor 69b determines the function unique to the capsule endoscope 2a, 2b which is a object which has taken the in-vivo images $P_{n-1}$, $P_n$ based on the time interval $\Delta T_{n-1}$ between the in-vivo image $P_{n-1}$ and $P_n$ calculated by the time calculator 29a substantially like the standard monocular capsule and the standard binocular capsule and identifies the in-vivo images $P_{n-1}$, $P_n$ depending on the determined functions.

According to the fourth embodiment, as described above, when transmitting the in-vivo images taken with one or more imaging units successively by radio to outside, the in-vivo images are transmitted successively by radio following order that the imaging units take images at a time interval corresponding to the function of the device classified depending on the number of possessed imaging units, frame rate, illumination light intensity and whether or not the image compression processing is to be executed and the like. Thus, the function unique to the device and the imaging unit for each in-vivo image can be notified to outside by the time interval between the in-vivo images transmitted successively by radio even if no identification information corresponding to the function unique to the device is attached to each image signal. As a result, the same operating effect as the first and second embodiments can be enjoyed and the in-vivo image acquiring apparatus capable of identifying the in-vivo images easily depending on the function unique to the device can be achieved without increasing the amount of information when the in-vivo images taken by one or more imaging units are transmitted by radio.

The in-vivo images of the subject which the in-vivo image acquiring apparatus transmits successively by radio are received successively, each time information which specifies the received in-vivo images is detected, a time interval of each in-vivo image is calculated based on the detected time information so as to acquire a time interval corresponding to the function unique to the in-vivo image acquiring apparatus and the imaging order and the in-vivo images of the subject are identified based on the acquired time interval. Consequently, the in-vivo images of the subject can be identified depending on the function unique to the in-vivo image acquiring apparatus and each imaging unit based on the time interval of the in-vivo images received successively even if no identification information indicating the function of the device is received from the in-vivo image acquiring apparatus. As a result, the same operating effect as the first and second embodiments can be enjoyed and the receiving apparatus capable of easily identifying the in-vivo images of the subject depending on the function unique to the in-vivo image acquiring apparatus and the imaging unit can be achieved without increasing the amount of information when the in-vivo images which the in-vivo image acquiring apparatus acquires with one or more imaging units are transmitted successively by radio.

Further, the same operating effect as the first and second embodiments can be enjoyed by providing the in-vivo image acquiring apparatus and the receiving apparatus and the in-vivo image acquiring system capable of acquiring the in-vivo images which can be identified easily depending on the function unique to the in-vivo image acquiring apparatus and the imaging unit can be achieved without increasing the amount of information when the in-vivo images of the subject taken by one or more imaging units are transmitted by radio.

Although according to the first to fourth embodiments of the present invention, the monocular capsule endoscope 2a having one imaging unit transmits the in-vivo images taken by the imaging unit 12a successively following an imaging order (that is, frame number order), the present invention is not limited to this example, but the capsule endoscope (in-vivo image acquiring apparatus) having one imaging unit may transmit the in-vivo images taken successively by this imaging unit successively following a desired frame order by radio. In this case, the transmitting order of the in-vivo images does not always need to follow the imaging order.

Although according to the first to fourth embodiments, the image (in-vivo image) at the first frame acquired by the capsule endoscope 2a, 2b is recorded in the portable recording medium 6, the present invention is not limited to this example, but the content of the image at the first frame is determined based on the time information (imaging time, receiving time and the like) of the images at the first frame and the second frame and the image at the first frame is recorded in the portable recording medium 6 if it is an image useful for examination of a subject, and if it is not a useful image, the image at the first frame may be aborted. In this case, the image at the first frame may be stored temporarily for the time calculator 29a to calculate a difference in time (time interval) of the images between at the first frame and at the second frame.

Further, although according to the first to fourth embodiments of the present invention, the receiving apparatus determines that the in-vivo image received from the capsule endoscope is an image at the first frame in a condition (that is, initialized condition) in which no in-vivo image is recorded in the portable recording medium mounted on the receiving apparatus, the present invention is not limited to this example, but if the time interval of the in-vivo images which the receiving apparatus receives is more than a predetermined threshold, it may determine that it is the in-vivo image at the first frame and if the time interval of the in-vivo image is not a time interval not registered on the data table 57a, it may determine that it is an in-vivo image at the first frame.

According to the first embodiment to fourth embodiment of the present invention, as the type of the capsule endoscope different in function, the standard monocular capsule, the high illumination monocular capsule, the high rate monocular capsule, the low rate monocular capsule, the standard binocular capsule, the high illumination binocular capsule, the low rate binocular capsule, the compression binocular capsule and the high rate binocular capsule are exemplified. The present invention is not limited to these examples but any monocular or compound eye endoscopes having diversified functions classified depending on the number of possessed imaging units, imaging frame rate, transmission frame rate, whether or not image compression processing is to be executed, illumination light intensity and the like may be used. In this case, the number of the imaging units possessed by the compound eye capsule endoscope may be three or more and the monocular capsule endoscope may be equipped with image compression processing function. If the function of the capsule endoscope is diversified, the time interval of the in-vivo images corresponding to the function of the capsule endoscope or its combination may be diversified or complicated.

Further although according to the first to fourth embodiment of the present invention, the in-vivo images are identified depending on the function unique to the capsule endoscope by attaching the identification information corresponding to the function unique to the capsule endoscope to each in-vivo image, the present invention is not limited to this example, but it is permissible to form a recording area such as a folder different depending on the function of the capsule endoscope in the portable recording medium 6 and record the in-vivo image in the recording area so as to identify each in-vivo image depending on the function unique to the capsule endoscope. In this case, it is permissible to attach the function of the capsule endoscope or a folder name for specifying the in-vivo image to a recording area (folder) different depending on the function of the capsule endoscope. Further, if the in-vivo images are identified depending on the function unique to the capsule endoscope, it is permissible to attach the identification information to the in-vivo image corresponding to the function unique to the capsule endoscope while no identification information is attached to the in-vivo image corresponding to the function of other capsule endoscope.

Although according to the first to fourth embodiment of the present invention, detection time of synchronous signal is exemplified as the time information of the in-vivo image, the present invention is not limited to this example, but the time information of the in-vivo image may be any time information capable of specifying the in-vivo image and for example, may be a receiving termination time of the in-vivo image in a frame unit or a time when the generation of the in-vivo image of the frame unit is terminated. In this case, the receiving unit may be provided with a time information detector for detecting a time when reception of the image signal in the frame unit by the antenna unit 4a is terminated (that is, time when the reception of the in-vivo image in the frame unit is terminated) or a time information detector for detecting a time when generation of the in-vivo image in the frame unit by the signal processor 25 is completed.

Further, in the first to fourth embodiment of the present invention, the capsule endoscope provided with the imaging unit for taking the in-vivo images and the radio unit for transmitting the in-vivo image by radio inside the capsule type casing is explained as an example of the in-vivo image acquiring apparatus, the present invention is not limited to this example, but any in-vivo image acquiring apparatus may be adopted as long as it includes an imaging unit for taking the in-vivo images and a communication unit for transmitting the in-vivo image to a receiving unit outside the subject.

The in-vivo image acquiring apparatus of the present invention, when transmitting the in-vivo images of the subject taken by one or more imaging units, transmits the in-vivo images successively at a time interval corresponding to the function unique to the device. Consequently, the function unique to the device can be notified to outside at the time interval of the in-vivo images transmitted successively by radio even if no identification information corresponding to the function of the device is attached to the image signal. As a result, the in-vivo images of the subject can be transmitted successively by radio and further the in-vivo images can be transmitted in a condition in which it can be identified depending on the function unique to the device without increasing the amount of information when each in-vivo image is transmitted by radio.

The receiving apparatus of the present invention receives the in-vivo images of the subject which the in-vivo image acquiring apparatus transmits successively by radio are in succession, detects each time information which specifies the received in-vivo images, calculates a time interval of each in-vivo image based on the detected time information so as to acquire a time interval corresponding to the function unique to the in-vivo image acquiring apparatus and identifies the in-vivo images of the subject based on the acquired time interval. Consequently, the in-vivo images of the subject can be identified depending on the function of the in-vivo image acquiring apparatus and each imaging unit based on the time interval of the in-vivo images received successively even if no identification information indicating the function of the device is received from the in-vivo image acquiring apparatus. As a result, the in-vivo images of the subject are received successively and the in-vivo image acquiring apparatus can identify the in-vivo images of the subject depending on the function of the in-vivo image acquiring apparatus without increasing the amount of information when the in-vivo images are transmitted by radio.

Further the in-vivo image acquiring system of the present invention can acquire the in-vivo images which can be identified depending on the function unique to the in-vivo image acquiring apparatus by providing such an in-vivo image acquiring apparatus and receiving apparatus, without increasing the amount of information when each in-vivo image of the subject is transmitted by radio.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A receiving apparatus comprising:
   a receiving unit for receiving in-vivo images of a subject, the in-vivo images being transmitted by radio by an in-vivo image acquiring apparatus for taking the in-vivo images with at least one imaging unit;
   a detecting unit for detecting time information concerning time when the in-vivo image is received or time relating to the receiving time; and
   a control unit for calculating a time interval between continuous in-vivo images of the in-vivo images based on the time information detected by the detecting unit and identifying a type of the in-vivo image acquiring apparatus based on the calculated time interval,
   wherein the control unit identifies the type of the in-vivo image acquiring apparatus based on a combination of the plural time intervals.

2. The receiving apparatus according to claim 1, further comprising a memory unit for storing therein a data table indicating a correspondence relationship between the combination of the time interval and the function or feature of the in-vivo image acquiring apparatus, wherein
   the control unit determines the type of the in-vivo image acquiring apparatus corresponding to the combination of the time intervals by referring to the data table and identifies the in-vivo images depending on the determined type of the in-vivo image acquiring apparatus.

3. The receiving apparatus according to claim 1, further comprising a recording unit in where the in-vivo image is recorded, wherein the control unit records the in-vivo images in the recording unit so that the in-vivo images are identified depending on the type of the in-vivo image acquiring apparatus.

4. The receiving apparatus according to claim 3, wherein the control unit attaches the identification information corresponding to the type of the in-vivo image acquiring apparatus to the in-vivo image and identifies the in-vivo images depending on the type of the in-vivo image acquiring apparatus.

5. The receiving apparatus according to claim 3, wherein the control unit controls the recording unit to record the in-vivo images depending on the type of the in-vivo image acquiring apparatus and identifies the in-vivo images depending on the type of the in-vivo image acquiring apparatus.

6. The receiving apparatus according to claim 1, further comprising a compressing unit for compressing the in-vivo image, wherein
the control unit determines whether the in-vivo image is a compressed image and if the in-vivo image is not a compressed image, controls the compressing unit to compress the in-vivo image.

7. An in-vivo image acquiring system comprising:
an in-vivo image acquiring apparatus which is introduced into an inside of a subject to take in-vivo images of the subject and transmits the in-vivo images of the subject successively by radio at a time interval depending on function or feature of the in-vivo image acquiring apparatus; and
a receiving apparatus which receives the in-vivo image transmitted successively by radio by the in-vivo image acquiring apparatus, detects each time information which specifies the received in-vivo image, calculates the time interval which is a difference of the time information between continuous in-vivo images of the in-vivo images, and identifies the in-vivo images depending on a type of the in-vivo image acquiring apparatus based on the calculated time interval, wherein the receiving apparatus comprises:
a receiving unit for receiving the in-vivo images transmitted by radio by the in-vivo image acquiring apparatus;
a detecting unit for detecting pieces of time information each specifying the in-vivo image;
a calculating unit for calculating the time interval which is a difference of the time information between the continuous in-vivo images of the in-vivo images; and
an identification processing unit for identifying the in-vivo images depending on the type of the in-vivo image acquiring apparatus corresponding to the time interval calculated by the calculating unit, wherein the identification processing unit identifies the in-vivo images depending on the type of the in-vivo image acquiring apparatus based on a combination of the plural time intervals.

8. The in-vivo image acquiring system according to claim 7, wherein the in-vivo image acquiring apparatus comprises a plurality of imaging units for taking the in-vivo images;
a transmitting unit for transmitting the in-vivo images taken by the imaging units to the receiving apparatus by radio; and
a control unit for controlling the imaging units to take the in-vivo images successively and controlling the transmitting unit to transmit the in-vivo images successively by radio at the time interval depending on the type of the in-vivo image acquiring apparatus following order that the imaging units take images.

9. The in-vivo image acquiring system according to claim 8, wherein the control unit compresses the in-vivo images and controls the transmitting unit to transmit the compressed in-vivo images successively by radio at the time interval depending on the compression processing function.

10. The in-vivo image acquiring system according to claim 7, wherein the receiving apparatus further comprises a memory unit for storing therein a data table indicating a correspondence relationship between a combination of the time interval and the type of the in-vivo image acquiring apparatus, wherein
the identification processing unit determines the type of the in-vivo image acquiring apparatus corresponding to a combination of the time intervals by referring to the data table and identifies the in-vivo image depending on the determined type of the in-vivo image acquiring apparatus.

11. The in-vivo image acquiring system according to claim 7, wherein the receiving apparatus further comprises a recording unit in which the in-vivo image is recorded, wherein
the identification processing unit records the in-vivo images in the recording unit in conditions in which the in-vivo images are identified depending on the type of the in-vivo image acquiring apparatus.

12. The in-vivo image acquiring system according to claim 11, wherein the identification processing unit attaches identification information corresponding to the type of the in-vivo image acquiring apparatus to the in-vivo images and identifies the in-vivo images depending on the type of the in-vivo image acquiring apparatus.

13. The in-vivo image acquiring system according to claim 11, wherein the identification processing unit records the in-vivo image in the recording unit depending on the type of the in-vivo image acquiring apparatus and identifies the in-vivo image depending on the type of the in-vivo image acquiring apparatus.

14. The in-vivo image acquiring system according to claim 7, further comprising a compressing unit for compressing the in-vivo image, wherein
the identification processing unit determines whether the in-vivo image is a compressed image and if the in-vivo image is not a compressed image, controls the compressing unit to compress the in-vivo image.

* * * * *